United States Patent [19]  [11] 4,095,021
Bradshaw et al.  [45] June 13, 1978

[54] 3-CARBAMOYLOXYMETHYL OR N-METHYL-CARBAMOYLOXYMETHYL-7-[2-CARBOXYMETHOXYIMINO-2-(FUR-2-YL OR THIEN-2-YL)ACETAMIDO]CEPH-3-EM-4-CARBOXYLIC ACIDS AND DERIVATIVES THEREOF

[75] Inventors: Janice Bradshaw, Harrow; Martin Christopher Cook, Liverpool; Gordon Ian Gregory, Chalfont St. Peter, all of England

[73] Assignee: Glaxo Laboratories Limited, Greenford, England

[21] Appl. No.: 668,244

[22] Filed: Mar. 18, 1976

Related U.S. Application Data

[62] Division of Ser. No. 533,451, Dec. 16, 1974, abandoned.

[30] Foreign Application Priority Data

Dec. 21, 1973 United Kingdom ............... 59517/73

[51] Int. Cl.² ................. C07D 501/34; A61K 31/545
[52] U.S. Cl. ..................................... 544/22; 424/246; 544/25; 544/27; 544/28; 544/17; 542/442; 260/347.4; 260/347.3; 260/332.2 A
[58] Field of Search ...................... 260/243 C; 544/22

[56] References Cited

FOREIGN PATENT DOCUMENTS

| | | |
|---|---|---|
| 804,450 | 4/1974 | Belgium. |
| 2,223,375 | 11/1972 | Germany. |
| 2,204,060 | 8/1972 | Germany. |
| 2,262,500 | 7/1973 | Germany. |
| 2,460,537 | 7/1975 | Germany. |
| 68,680 | 1/1974 | Luxembourg. |

Primary Examiner—Donald G. Daus
Assistant Examiner—Diana G. Rivers
Attorney, Agent, or Firm—Bacon & Thomas

[57] ABSTRACT

Cephalosporin antibiotics in which the 7β-acylamido group has the structure

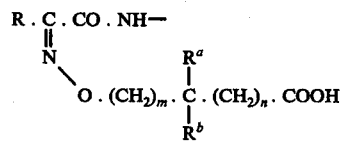

(where R is thienyl or furyl; $R^a$ and $R^b$ are each selected from hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl and cyano, or $R^a$ and $R^b$ together with the carbon atom to which they are attached form a $C_{3-7}$ cycloalkylidene or cycloalkenylidene group; and $m$ and $n$ are each 0 or 1 such that the sum of $m$ and $n$ is 0 or 1) exhibit broad spectrum antibiotic activity characterized by particularly high activity against gram negative microorganisms, including those which produce β-lactamases. The compounds, which are syn isomers or exist as mixtures of syn and anti isomers containing at least 90% of the syn isomer, have particularly high in vitro activity against strains of Escherichia coli, Haemophilus influenzae and Proteus organisms; compounds wherein at least one of $R^a$ and $R^b$ is other than hydrogen have also shown unusually high activity against Pseudomonas organisms. Important compounds of the above type include those in which the 7β-acylamido group is a syn-2-carboxymethoxy-2-(fur-2-yl)acetamido, syn-2-(2-carboxyprop-2-yloxyimino)-2-(fur-2-yl)acetamido or syn-2-(1-carboxycyclopent-1-yloxyimino)-2-(fur-2-yl)acetamido group.

4 Claims, No Drawings

3-CARBAMOYLOXYMETHYL OR N-METHYL-CARBAMOYLOXYMETHYL-7-[2-CARBOXYMETHOXYIMINO-2-(FUR-2-YL OR THIEN-2-YL)ACETAMIDO]CEPH-3-EM-4-CARBOXYLIC ACIDS AND DERIVATIVES THEREOF

This is a division of application Ser. No. 533,451, filed Dec. 16, 1974, now abandoned.

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are an increasingly common source of infection in humans, and are also generally substantially inactive against Pseudomonas organisms. Several Pseudomonas organisms are resistant to the majority of existing commercially available antibiotic compounds, and the practical therapeutic applications of aminoglycoside antibiotics such as gentamicin which do exhibit Pseudomonas activity tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of Proteus and Pseudomonas fulfils a significant need in chemotherapy.

The present invention provides 7β-acylamidoceph-3-em-4-carboxylic acid antibiotics and non-toxic derivatives thereof which are characterised in that the said acylamido moiety has the formula

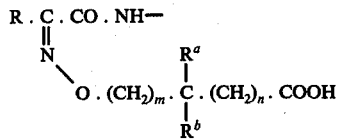

[wherein R is a thienyl or furyl group; $R^a$ and $R^b$, which may be the same or different, are each selected from hydrogen, $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, napthyl, thienyl, furyl, carboxy, $C_{2-5}$ alkoxycarbonyl (e.g. ethoxycarbonyl) and cyano, or $R^a$ and $R^b$ together with the carbon atom to which they are attached form a $C_{3-7}$ cycloalkylidene or cycloalkenylidene group (e.g. a cyclobutylidene, cyclopentylidene or cyclohexylidene group); and $m$ and $n$ are each 0 or 1 such that the sum of $m$ and $n$ is 0 or 1], the compounds being syn isomers or existing as mixtures of syn and anti isomers containing at least 90% of the syn isomer.

These compounds exhibit broad spectrum antibiotic activity characterised by particularly high activity against gram negative microorganisms, including those which produce β-lactamases, and also possess very high stability to β-lactamases produced by a range of gram negative organisms. A characteristic feature of the compounds is their high in vitro activity against gram-negative organisms such as *Enterobacter clocae, Serratia marcescens* and *Klebsiella aerogenes*. The compounds have particularly high activity against strains of *Escherichia coli, Haemophilus influenzae* and Proteus organisms, e.g. strains of *Proteus morganii* and *Proteus mirabilis*. Compounds wherein at least one of $R^a$ and $R^b$ is other than hydrogen have also shown unusually high activity against Pseudomonas organisms, for example strains of *Pseudomonas aeruginosa*.

The compounds of the invention are defined as having the syn isomeric form as regards the configuration of the group

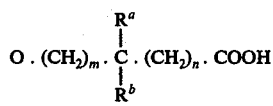

with respect to the carboxamido group. In this specification the syn configuration is denoted structurally as

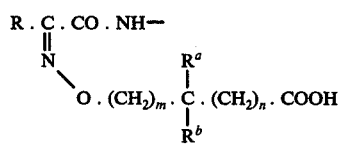

this configuration being assigned on the basis of the work of Ahmad and Spenser reported in *Can. J. Chem.*, 1961, 39, 1340. As indicated above, the compounds may exist as mixtures of syn and anti isomers provided that such mixtures contain at least 90% of the syn isomer. We prefer, however, the compounds to be syn isomers essentially free from the corresponding anti isomer.

The antibiotic compounds of the invention therefore comprise compound of the general formula:

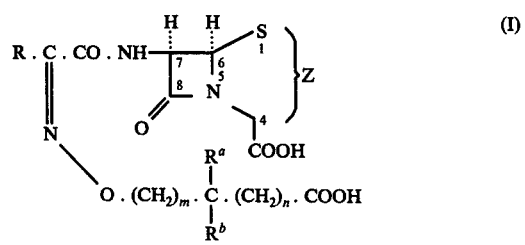

(wherein R, $R^a$, $R^b$, $m$ and $n$ have the above-defined meanings and Z is a group in which 2 carbon atoms link the nuclear sulphur atom and the 4-position carbon atom such that the compound possesses Δ³ olefinic unsaturation) and non-toxic derivatives thereof.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction of either or both of the carboxyl groups present in the compound of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives wich may be formed from compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The inventon embraces the individual diastereoisomers of such compounds as well as mixtures thereof.

The cephalosporin antibiotics according to the present invention may be substituted at the 3-position by any of the wide range of substituents disclosed in the literature pertaining to cephalosporin compounds, the characterising feature of the invention being the nature of the 7β-acylamido group. The invention thus includes within its scope compounds of the general formula:

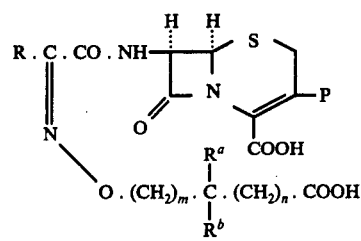

[where R, $R^a$, $R^b$, m and n are hereinbefore defined and P represents an organic group, for example a saturated or unsaturated, substituted or unsubstituted, organic group containing 1–20 carbon atoms] and non-toxic derivatives thereof.

Where P is an unsaturated organic group it may, for example, be a group of the formula

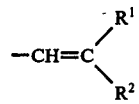

wherein $R^1$ and $R^2$, which may be the same or different, are each selected from hydrogen, carboxy, cyano, $C_{2-7}$ alkoxycarbonyl (e.g. methoxycarbonyl or ethoxycarbonyl), and substituted or unsubstituted aliphatic (e.g. alkyl, preferably $C_1$–$C_6$ alkyl such as methyl, ethyl, iso-propyl or n-propyl), $C_5$–$C_7$ cycloaliphatic (e.g. $C_{5-7}$ cycloalkyl such as cyclopentyl or cyclohexyl), $C_7$–$C_{10}$ araliphatic (e.g. phenyl $C_{1-4}$ alkyl such as benzyl or phenylethyl) and $C_6$–$C_{12}$ aromatic (e.g. mono- or bicyclic carbocylic aryl such as phenyl, nitrophenyl, tolyl or napthyl) groups. Specific substituted vinyl groups of the above formula include 2-carboxyvinyl, 2-methoxycarbonylvinyl, 2-ethoxycarbonylvinyl and 2-cyanovinyl.

P may also be a substituted methyl group, which may be depicted by the formula

—CH₂Y where Y is an atom or group, e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines, for example tri($C_{1-6}$ alkyl) amines such as triethylamine, and heterocyclic tertiary amines. The heterocyclic tertiary amines may if desired contain one or more further heteroatoms in addition to the basic nitrogen atom, and may be substituted or unsubstituted. The heterocyclic tertiary amine may thus, for example, be a pyridine, pyrimidine, pyridazine, pyrazine, pyrazole, imidazole, triazole or thiazole; a fused bi- or poly-cyclic analogue of any of these heterocycles, for example purine or benzotriazole; and any of the above amines substituted by one or more aliphatic (e.g. lower alkyl such as methyl, ethyl, n-propyl or isopropyl), aryl (e.g. $C_{6-12}$ mono- or bicyclic carbocyclic aryl such as phenyl or naphthyl), araliphatic (e.g. phenyl lower alkyl such as benzyl or phenylethyl), lower alkoxymethyl (e.g. methoxymethyl, ethoxymethyl, n-propoxymethyl or iso-propoxymethyl), acyloxymethyl (e.g. lower alkanoyloxymethyl such as acetoxymethyl), formly, acyloxy (e.g. lower alkanoyloxy such as acetoxy), carboxy, esterified carboxy (e.g. lower alkoxycarbonyl such as methoxycarbonyl), carboxy lower alkyl (e.g. carboxymethyl), sulpho, lower alkoxy (e.g. methoxy, ethoxy, n-propoxy or iso-propoxy), aryloxy (e.g. phenoxy), aralkoxy (e.g. benzyloxy), alkylthio (e.g. methylthio or ethylthio), arylthio, aralkylthio, cyano, hydroxy, carbamoyl, N-monoloweralkylcarbamoyl (e.g. N-methylcarbamoyl or N-ethylcarbamoyl), N,N-diloweralkylcarbamoyl (e.g. N,N-dimethylcarbamoyl or N,N-diethylcarbamoyl), N-(hydroxyloweralkyl)carbamoyl (e.g. N-(hydroxymethyl)carbamoyl or N-(hydroxyethyl)carbamoyl), or carbamoyllowralkyl (e.g. carbamoylmethyl or carbamoylethyl) groups. Examples of Y groups which may be obtained from heterocyclic tertiary amine nucleophiles of the above type include pyridinium, 3 - and 4-carbamoylpyridinium, 3-carboxymethylpyridinium, 3-sulphopyridinium, thiazol-3-yl, pyrazol-1-yl, pyridazinium, and benzotriazol-1yl.

Another class of nitrogen nucleophiles comprises azides, e.g. alkali metal azides such as sodium azide.

When the group Y is a derivative of a residue of a nitrogen nucleophile it may be, for example, an amino group or an acylamido group. Compounds in which Y is amino may be derived from the corresponding compound in which Y is azido by reduction, e.g. by catalytic hydrogenation of the azide using a precious metal catalyst such as palladium or platinum. Compounds in which Y is an acylamido group may be derived by acylation of a compound wherein Y is amino, e.g. by any method suitable for acylating an aminocephalosporin, for example reaction of the amino compound with an acid chloride, acid anhydride or mixed anhydride of an acid corresponding to the desired acyl group and another acid.

Compounds wherein Y is amino may also be reacted with a substituted isocyanate or isothiocyanate to yield urea or thiourea derivatives.

Other compounds in which Y is a derivative of a residue of a nitrogen nucleophile may be obtained by reacting a compound in which Y is azido with a dipolarophile. Examples of suitable dipolarophiles include acetylenic, ethylenic and cyano dipolarophiles.

Acetylenic dipolarophiles may be shown as having the structure

wherein $R^3$ and $R^4$, which may be the same or different, are atoms or groups.

In general we prefer that $R^3$ and preferably also $R^4$ should be of an electronegative nature. Examples of such groups include cyano, $CO_2R^5$, $COR^5$ (where $R^5$ is, for example, hydrogen, lower alkyl, aryl or lower aralkyl), and trihalomethyl e.g. trifluoromethyl.

However, $R^3$ and preferably also $R^4$ could be electropositive e.g. alkoxy or alkylamino.

$R^3$ and $R^4$ may together form a ring system with the acetylenic group such as, for example, in an aryne.

Where $R^3$ and $R^4$ are discrete atoms or groups which are identical a single compound will result on reaction with the azido cephalosporin; if they are different one will in general obtain a mixture of position isomers.

Ethylenic dipolarophiles may be shown as having the structure

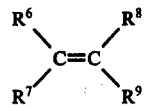

where $R^6$, $R^7$, $R^8$ and $R^9$ which may be the same or different are atoms or groups. Although $R^6$, $R^7$, $R^8$ and $R^9$ may all be hydrogen, ethylene per se, like acetylene, reacts sluggishly with azido groups. $R^6$ and $R^8$ may together form a cyclic structure, e.g. a carbocyclic structure, with the ethenoid group such that the double bond is strained. Examples of ethylenic dipolarophiles containing strained double bonds include norbornenes, transcycloalkenes and acenaphthalene.

Further ethylenic dipolarophiles which may be used include compounds of the formula $R^6$. $R^7C = CR^8$. $R^9$ where at least one of $R^6$, $R^7$, $R^8$ and $R^9$ is an electronegative group. $R^6$ and $R^8$ may thus be identical electronegative groups, $R^7$ and $R^9$ being other groups as desired. $R^7$ and $R^9$ may thus together form a ring system. Examples of such dipolarophiles include benzoquinone and nuclear substituted benzoquinones and maleimide. Again all of $R^6$, $R^7$, $R^8$ and $R^9$ may be identical electronegative groups. Electronegative groups which may be used include those listed under the section on acetylenic dipolarphiles and examples of such compounds thus include dicyanoethylene and lower mono- and di-alkoxycarbonyl ethylenes.

One or more of $R^6$, $R^7$, $R^8$ and $R^9$ may if desired be electropositive.

Cyano compounds, especially those which are activated by electronegative groups, may function as cyano dipolarophiles. Examples of such dipolarophiles include lower alkoxycarbonyl cyanides and cyanogen.

CARBON NUCLEOPHILES

Examples of carbon nucleophiles include inorganic cyanides, pyrroles and substituted pyrroles, e.g. indoles, and compounds giving stabilised carbanions, for example acetylenes and compounds having β-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substituent a group of the formula

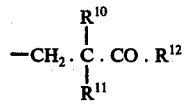

wherein $R^{10}$ and $R^{11}$, which may be the same or different, are selected from hydrogen; cyano; lower alkyl e.g. methyl or ethyl; phenyl; phenyl substituted by, for example, halo, lower alkyl, lower alkoxy, nitro, amino or lower alkylamino; carboxy; lower alkoxycarbonyl; mono- or di-aryl lower alkoxycarbonyl; lower alkylcarbonyl; aryl lower alkyl or $C_5$ or $C_6$ cycloalkyl and $R^{12}$ is selected from hydrogen; lower alkyl e.g. methyl or ethyl; phenyl; phenyl substituted by, for example, halo, lower alkyl, lower alkoxy, nitro, amino or lower alkylamino; aryl lower alkyl or $C_5$ or $C_6$ cycloalkyl.

SULPHUR NUCLEOPHILES

Examples of sulphur nucleophiles include thioureas, including aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

One class of sulphur nucleophile includes those compounds of the formula: $R^{13}.S(O)_nH$ in which $R^{13}$ is an aliphatic e.g. lower alkyl such as methyl, ethyl or n-propyl group; an alicyclic e.g. lower cycloalkyl such as cyclohexyl or cyclopentyl group; an aromatic e.g. $C_{6-12}$ mono- or bicyclic carbocyclic aryl such as phenyl or naphthyl group; an araliphatic e.g. phenyl lower (e.g. $C_{1-4}$) alkyl such as benzyl group; or a heterocyclic group, and $n$ is 0, 1 or 2. A preferred class of nucleophiles falling within the above formula is that having the general formula $R^{14}SH$ in which $R^{14}$ is aliphatic, e.g. lower alkyl such as methyl, ethyl or n-propyl or lower alkanoyl such as acetyl; araliphatic, e.g. phenyl lower alkyl such as benzyl or phenethyl or substituted phenyl lower alkyl; alicyclic, e.g. cycloalkyl such as cyclopentyl or cyclohexyl; aromatic, e.g. phenyl, substituted phenyl or a heterocyclic group containing at least one 5 - or 6-membered ring and having one or more heteroatoms selected from O, N and S. Such heterocyclic groups $R^{14}$ may be substituted, and examples of suitable heterocyclic groups includes thiadiazolyl, e.g. 5-methyl-1,3,4-thiadiazol-2-yl; diazolyl; triazolyl, e.g. triazol-4-yl; tetrazolyl, e.g. 1-methyltetrazol-5-yl, 1-ethyltetrazol-5-yl or 1-phenyltetrazol-5-yl; thiazolyl; thiatrizolyl; oxazolyl; oxadiazolyl, e.g. 2-phenyl-1,3,4-oxadiazol-5-yl; pyridyl, e.g. N-methylpyrid-2-yl; pyrimidyl; fused heterocyclic ring systems such as benzimidazolyl, benzoxazolyl, benzothiazolyl such as benzothiazol-2-yl, triazolopyridyl or purinyl; and substituted versions of such fused ring systems, e.g. nitrobenzothiazol-2-yl such as 5- or 6-nitrobenzothiazol-2-yl.

OXYGEN NUCLEOPHILES

Examples of oxygen nucleophiles include water; alcohols, for example alkanols such as methanol, ethanol, propanol and butanol; and lower alkanoic and alkenoic acids The term "oxygen nucleophile" thus includes compounds of the following formula:

in which the group $R^{15}$ may be lower alkyl (e.g. methyl, ethyl, n-propyl, isopropyl, n-butyl or isobutyl); lower alkenyl (e.g. allyl); lower alkynyl (e.g. propynyl); lower cycloalkyl (e.g. cyclopropyl, cyclopentyl or cyclohexyl); lower cycloalkyl lower alkyl (e.g. cyclopropylmethyl, cyclopentylmethyl or cyclohexylethyl); aryl (e.g. phenyl or naphthyl); aryl lower alkyl (e.g. benzyl); heterocyclic(e.g. a heterocyclic group as defined for $R^{14}$, such as N-methylpyrid-2-yl); heterocyclic lower alkyl (e.g. furfuryl); or any of these groups substituted by, for example, one or more of lower alkoxy (e.g. methoxy or ethoxy), lower alkylthio (e.g. methylthio or ethylthio), halogen (chlorine, bromine, iodine or fluorine), lower alkyl (e.g. methyl or ethyl), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which water is the nucleophile there will be obtained 3-hydroxymethyl cephalosporin compounds. Such 3-hydroxymethyl compounds and non-toxic derivatives thereof may show antibacterial activity and it is of note that they may be metabolites of compounds of general formula II where P is acetoxymethyl. 3-Hydroxymethyl cephalosporins may be acylated to form derivatives characterized by possessing the group $3-CH_2.O.CO.R^{16}$ or $3-CH_2.O.CO.AR^{17}$ where A is O, S or NH, $R^{16}$ is an organic group and $R^{17}$ is hydrogen or an organic group.

The group $R^{16}CO-$ or $R^{17}A.CO-$ may be chosen from among the wide class of such groups described in the literature and may have up to 20 carbon atoms. $R^{16}$ and, where appropriate, $R^{17}$ may thus each be a hydrocarbon group or such a group carrying one or more substituent atoms or groups, and may thus be chosen from the following list, which is not intended to be exhaustive:

(i) $C_nH_{2n+1}$ where $n$ is an integer from 1 to 7, e.g. 1 to 4. The group may be straight or branched and, if desired, may be interrupted by an oxygen or sulphur atom or an imino group or substituted by cyano, carboxy, lower alkoxycarbonyl, hydroxy, carboxycarbonyl (HOOC.CO.), halogen (e.g. chlorine, bromine or iodine) or amino. Examples of such groups include methyl, ethyl, propyl, isopropyl, n-butyl, t-butyl, sec.-butyl and 2-chloroethyl.

(ii) $C_nH_{2n-1}$ where $n$ is an integer from 2 to 7. The group may be straight or branched and, if desired, may be interrupted by an oxygen or sulphur atom or an imino group. Examples of such groups include vinyl and propenyl.

(iii) $R^{18}$, where $R^{18}$ is carbocyclic aryl (e.g. $C_{6-12}$ mono- or bicyclic carbocyclic aryl), heterocyclic aryl (e.g. comprising a 5- or 6-membered ring containing at least one of O, N and S), lower cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and 3-yl; pyridyl; cyclohexyl; cyclopentyl; cyclopropyl; sydone; naphthyl; and substituted naphthyl e.g. 2-ethoxynaphthyl.

(iv) $R^{18}(CH_2)_m$ where $R^{18}$ has the meaning defined above under (iii) and $m$ is an integer from 1 to 4. Examples of this group include methyl, ethyl or butyl substituted by the various specific $R^{18}$ groups listed under (iii), e.g. lower cycloalkyl $C_{1-4}$ alkyl and carbocyclic or heterocyclic aryl $C_{1-4}$ alkyl such as benzyl and the appropriate substituted benzyl groups.

3-Position substituents of the above type thus include lower alkanoyloxymethyl groups such as acetoxymethyl and isobutyryloxymethyl, lower alkenoyloxymethyl groups such as crotonyloxymethyl; aroyloxymethyl groups such as benzoyloxymethyl; carbamoyloxymethyl, N-(lower alkyl)carbamoyloxymethyl such as N-methylcarbamoyloxymethyl, and N-(haloalkyl)carbamoyloxymethyl such as N-(2-chloroethyl)carbamoyloxymethyl.

A further important class of cephalosporin compounds are those possessing the group $3-CH_2Hal$ wherein Hal is chlorine, bromine or iodine. Such compounds may be primarily of value as intermedites of use in the preparation of active cephalosporin compounds by replacement of the halogen atom by a nucleophile e.g. a nitrogen-, oxygen- or sulphur-containing nucleophile as hereinbefore described.

The term "lower" as used in this specification and the accompanying claims to qualify aliphatic groups denotes, unless otherwise stated, that the said group may contain up to 6 carbon atoms. "Lower" as used to qualify cycloaliphatic groups indicated that the group may contain 3-7 (e.g. 5-7) carbon atoms.

A particularly interesting class of cephalosporin antibiotics in accordance with the invention comprises compounds of general formula

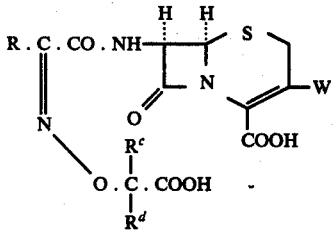

[wherein R is as hereinbefore defined, $R^c$ represents methyl, ethyl, propyl, allyl or phenyl and $R^d$ represents hydrogen, carboxy or, more preferably, a group as defined for $R^c$; or $R^c$ and $R^d$ together with the carbon atom to which they are attached form a cyclobutylidene, cyclopentylidene or cyclohexylidene group; and W is selected from:

(i) acetoxymethyl,
(ii) benzoyloxymethyl,
(iii) carbamoyloxymethyl
(iv) N-methylcarbamoyloxymethyl,
(v) a group of formula

(where $R^z$ represents cyano, carboxy or a $C_{2-5}$ alkoxycarbonyl group such as methoxycarbonyl or ethoxycarbonyl),
(vi) the group —$CH_2G$ where G is the residue of a nitrogen nucleophile selected from compounds of the formula

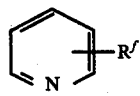

(wherein $R^f$ is hydrogen, carbamoyl, carboxymethyl or sulpho), and pyridazine,
(vii) azidomethyl, and
(viii) the group —$CH_2SR^w$ wherein $R^w$ is selected from pyridyl, diazolyl, triazolyl, tetrazolyl, thiazolyl, thiadiazolyl, oxadiazolyl, and substituted (e.g. lower alkyl- or phenyl-substituted) versions of these groups such as N-methylpyrid-2-yl, 1-methyltetrazol-5-yl, 1-phenyltetrazol-5-yl; 5-methyl-1,3,4-thiadiazol-2-yl and 5-phenyl-1,3,4-oxadiazol-2-yl]
and non-toxic derivatives thereof.

These compounds exhibit broad spectrum antibiotic activity (including very high activity against strains of Haemophilus influenzae and Proteus organisms) and high β-lactamase stability and are further characterised by particularly high in vitro activity against Psuedomonas organisms such as strains of Pseudomonas aeruginosa.

Especially preferred compounds of the above type, by virtue of their particularly high levels of activity against Proteus and Pseudomonas organisms, include the following:

(6R,7R)-7-[2-(2-carboxyprop-2-yloxyimino)-2-(fur-2-yl)acetamido]-3-pyridiniummethylceph-3-em-4-carboxylic acid (syn isomer), (6R,7R)-7-[2-(2-carboxyprop-2-yloxyimino)-2-(fur-2-yl)acetamido]-3-(5-methyl-1,3,4-thiadiazol-2-ylthiomethyl)ceph-3-em-4-carboxylic acid (syn isomer), (6R,7R)-3-carbamoyloxymethyl-7-[2-(2-carboxyprop-2-yloxyimino)-2-(fur-2-yl)acetamido]ceph-3-em-4-carboxylic acid (syn isomer), (6R,7R)-7-[2-(2-carboxyprop-2-yloxyimino)-2-(fur-2-yl)acetamido]-3-(trans-2-methoxycarbonylvinyl)-ceph-3-em-4-carboxylic acid (syn isomer), (6R,7R)-7-[2-(2-carboxyprop-2-yloxyimino)-2-(fur-2-yl)acetamido]-3-pyradiziniummethylceph-3-em-4-carboxylic acid (syn isomer), (6R,7R)-3-acetoxymethyl-7-[2-(1-carboxycyclopent-1-yloxyimino)-2-(fur-2-yl)acetamido]ceph-3-em-4-carboxylic acid (syn isomer), (6R,7R)-7-[2-(1-carboxycyclopent-1-yloxyimino)-2-(fur-2-yl)acetamido]-3-pyridiniummethylceph-3-em-4-carboxylic acid (syn isomer), (6R,7R)-7-[2-(1-carboxycyclopent-1-yloxyimino)-2-(fur-2-yl)acetamido]-3-(trans-2-carboxyvinyl)ceph-3-em-4-carboxylic acid (syn isomer), (6R,7R)-7-[2-(1-carboxycyclopent-1-yloxyimino)-2-(fur-2-yl)acetamido]-3-(1-methyltetrazol-5-ylthiomethyl)ceph-3-em-4-carboxylic acid (syn isomer), (6R,7R)-3-carbamoyloxymethyl-7-[2-(1-carboxycyclopent-1-yloxyimino)-2-(fur-2-yl)acetamido]ceph-3-em-4-carboxylic acid (syn isomer), (6R,7R)-3-acetoxymethyl-7-[2-(1-carboxybut-3-enyloxyimino)-2-(fur-2-yl)acetamido]ceph-3-em-4-carboxylic acid (syn isomer), (6R,7R)-3-acetoxymethyl-7-[2-(1-carboxycyclobut-1-yloxyimino)-2-(fur-2-yl)acetamido]ceph-3-em-4-carboxylic acid (syn isomer), (6R,7R)-7-[2-(1-carboxycyclobut-1-yloxyimino)-2-(fur-2-yl)acetamido]-3-pyridiniummethylceph-3-em-4-carboxylic acid (syn isomer), (6R,7R)-7-[2-(1-carboxycyclobut-1-yloxyimino)-2-(fur-2-yl)acetamido]-3-(1-methyltetrazol-5-ylthiomethyl)ceph-3-em-4-carboxylic acid (syn isomer), (6R,7R)-3-carbamoyloxymethyl-7-[2-(1-carboxycyclobut-1-yloxyimino)-2-(fur-2-yl)acetamido]ceph-3-em-4-carboxylic acid (syn isomer), (6R,7R)-3-acetoxymethyl-7-[2-(1-carboxypropoxyimino)-2-(fur-2-yl)acetamido]ceph-3-em-4-carboxylic acid (syn isomer), (6R,7R)-3-acetoxymethyl-7-[2-(3-carboxypent-3-yloxyimino)-2-(fur-2-yl)acetamido]ceph-3-em-4-carboxylic acid (syn isomer), (6R,7R)-3-acetoxymethyl-7-[2-(2-carboxyprop-2-yloxyimino)-2-(thien-2-yl)acetamido]ceph-3-em-4-carboxylic acid (syn isomer), and non-toxic derivatives thereof, e.g. alkali metal salts such as the sodium or potassium salts.

A further interesting class of cephalosporin antibiotics in accordance with the invention comprises componds of general formula

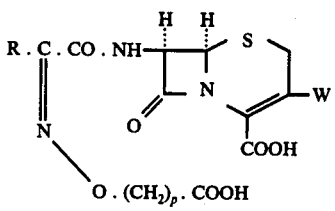

(IV)

[wherein R and W are as hereinbefore defined and p is 1 or 2] and non-toxic derivatives thereof.

These compounds exhibit broad spectrum antibiotic activity coupled with high β-lactamase stability. A characteristic feature of the compounds is their high activity against strains of *Haemophilus influenzae* coupled with their particularly high activity against strains of *Escherichia coli* and Proteus organisms.

Especially preferred compounds of the above type, by virtue of their particularly high levels of activity against *Escherichia coli* and Proteus organisms, include the following:

(6R,7R)-3-acetoxymethyl-7-[2-carboxymethoxyimino-2-(fur-2-yl)acetamido]ceph-3-em-4-carboxylic acid (syn isomer), (6R,7R)-3-azidomethyl-7-[2-carboxymethoxyimino-2-(fur-2-yl)acetamido]ceph-3-em-4-carboxylic acid (syn isomer), (6R,7R)-7-[2-carboxymethoxyimino-2-(fur-2-yl)acetamido]-3-(1-methyltetrazol-5-ylthiomethyl)-ceph-3-em-4-carboxylic acid (syn isomer), (6R,7R)-3-carbamoyloxymethyl-7-[2-carboxymethoxyimino-2-(fur-2-yl)acetamido]-ceph-3-em-4-carboxylic acid (syn isomer), and non-toxic derivatives thereof, e.g. alkali metal salts such as the sodium or potassium salts.

The compounds according to the invention may be prepared by any conventional method, for example by techniques analagous to those described in Belgian Pat. No. 783,449.

Thus according to one embodiment of the invention we provide a process for the preparation of an antibiotic compound of general formula I as hereinbefore defined or a non-toxic derivative thereof which comprises either (A) condensing a compound of the formula

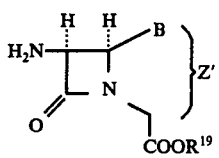

(V)

[wherein B is $>S$ or $>S\rightarrow O$ (α- or β-); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1-20 carbon atoms) or a symmetrical or mixed anhydride group derived from an appropriate acid; and Z' is a group in which 2 carbon atoms link the nuclear sulphur atom and the 4-position carbon atom so that the compound possesses $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acylating agent corresponding to an acid of formula

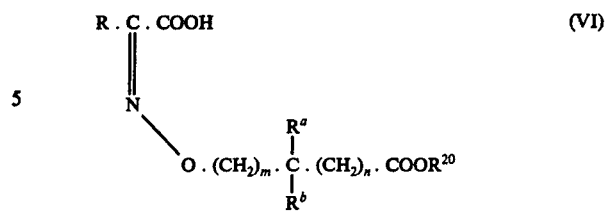

(VI)

(wherein $R,R^1,R^b,m$ and $n$ are as hereinbefore defined and $R^{20}$ is a carboxyl blocking group, e.g. a group as hereinbefore defined in connection with $R^{19}$); or (B), where Z in formula I is the group

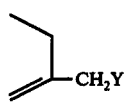

(where Y is as hereinbefore defined) reacting a compound of the formula

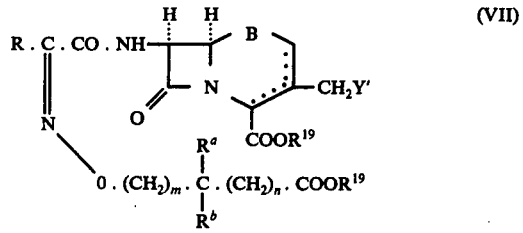

(VII)

(wherein $B,R,R^a,R^b,m$ and $n$ are as hereinbefore defined; each $R^{19}$ may independently represent hydrogen or a carboxyl blocking group; Y' is a replaceable residue of a nucleophile, e.g. an acetoxy or dichloroacetoxy group or a halogen atom such as chlorine, bromine or iodine; and the dotted line bridging the 2-, 3- and 4-positions indicates that the compound is a ceph-2-em or ceph-3-em compound) with a nucleophile; whereafter, if necessary and/or desired in each instance, any of the following reactions (C) in any appropriate sequence, are carried out:

(i) conversion of a $\Delta^2$ isomer into the desired $\Delta^3$ isomer, (ii) reduction of a compound wherein B is $>S\rightarrow O$ to form a compound wherein B is $>S$, (iii) reduction of a 3-azidomethyl compound to form a 3-aminomethyl compound, (iv) acylation of a 3-aminomethyl compound to form a 3-acylaminomethyl compound, (v) reaction of a 3-azidomethyl compound with a dipolarophile to form a compound having a polyazole ring linked to the 3-position carbon atom through a methylene group, (vi) deacylation of a 3-acyloxymethyl compound to form a 3-hydroxymethyl compound, (vii) acylation of a 3-hydroxymethyl compound to form a 3-acyloxymethyl compound, (viii) carbamoylation of a 3-hydroxymethyl compound to form an unsubstituted or substituted 3-carbamoyloxymethyl compound, and (ix) removal of carboxyl blocking groups;

and finally (D) recovering the desired compound of formula I or a non-toxic derivative thereof, if necessary after separation of isomers.

Non-toxic derivatives of the compound of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (VI) or a salt thereof with a halogenating agent e.g. phosphorus pentachloride, thionyl chloride or oxalyl chloride. Treatment of the sodium, potassium or triethylammonium salt of the acid (VI) with oxalyl chloride is advantageous in that under these conditions isomerisation is minimal.

Acylations employing acid halides may be effected in aqueous and non-aqueous reaction media, conveniently at temperatures of from $-50°$ to $+50°$ C, preferably $-20°$ to $+30°$ C, if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula VI may themselves be used as acylating agents in the preparation of compounds of formula I. Acylations employing acids (VI) are desirably conducted in the presence of a condensation agent, for example a carbodiimide such as N,N'-diethyl-, dipropyl- or diisopropylcarbodiimide, N,N'-dicyclohexylcarbodiimide or N-ethyl-N'-γ-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula VI such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline.

Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein $R^a$ or $R^b$ represents carboxy it will in many instances be necessary to protect the carboxy group, for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

Thus, for example, compounds substituted at the 3-position by a group $$-CH_2Y$$

wherein Y represents an ether or thioether group or a halogen atom may be prepared as described in British Pat. Nos. 1,241,656; 1,241,657; 1,277,415 and 1,279,402. Compounds wherein Y is the residue of a nucleophile may also be prepared by the reaction of a 3-acetoxymethyl cephalosporin compound with a nucleophile, for example pyridine or other tertiary amine as described in British Pat. No. 912,541; a sulphur-linking, nitrogen-linking or inorganic nucleophile as described in British Pat. No. 1,012,943; a sulphur-linking nucleophile as described in British Pat. Nos. 1,059,562; 1,101,423 and 1,206,305; or a nitrogen-linking nucleophile as described in British Pat. Nos. 1,030,630; 1,082,943 and 1,082,962. Compounds in which Y is a derivative of a residue of a nucleophile, e.g. where Y is an amino or acylamido group derived from an azido group may be prepared as described in British Pat. Nos. 1,057,883 and 1,211,694, these patents further describing the reaction of compounds in which Y is azido with a dipolarophile. Compounds wherein Y is the residue of a nucleophile may also be prepared by the reaction of a 3-halomethylcephalosporin with any of the nucleophiles disclosed in the above references, such a process being described in British Pat. No. 1,241,657, or by the reaction of a 3-halomethylcephalosporin sulphoxide with any of the nucleophiles disclosed in the above references, such a process being described in British Pat. No. 1,326,531. The contents of the above mentioned British Patents are herein incorporated for reference purposes.

Where a 3-halomethylcephalosporin sulphide or sulphoxide ester is reacted with a tertiary nitrogen nucleophile such as pyridine in accordance with the process of British Pat. Nos. 1,241,657 or 1,326,531, the reaction product will usually be obtained in the form of, for example, the corresponding 3-pyridiniummethyl halide. It has been observed that deesterification of compounds of this type by treatment with trifluoroacetic acid tends to promote isomerisation of the oxyimino moiety in the 7β-acylamido side chain; such isomerisation is clearly undesirable if a product containing at least 90% of the syn isomer is to be obtained without the need for a subsequent isomer separation stage.

It has also been observed, however, that the tendency to isomerisation may be substantially lessened if the 3-pyridiniummethyl halide is converted into the 3-pyridiniummethyl salt of a non-hydrohalic acid (e.g. trifluoroacetic, acetic, formic, sulphuric, nitric or phosphoric acid) prior to deesterification. Conversion of the halide salt into a non-hydrohalic acid salt is conveniently effected by means of anion exchange. This may be brought about by, for example, use of a suitable anion exchange resin, for example in the trifluoroacetate form. Where an anion exchange resin is employed, the 3-pyridiniummethyl halide may be run through a column of the resin prior to deesterification. Where the 3- pyridiniummethyl cephalosporin compound is a sulphide it may be advantageous to employ an inert organic solvent system (i.e. one which does not have a harmful effect on the resin) to ensure adequate solubility for the cephalosporin compound; organic solvent systems which may be used include lower alkanols such as ethanol, ketones such as acetone, and nitriles such as acetonitrile. Where the 3-pyridiniummethyl cephalosporin compound is a sulphoxide it may be preferable to employ an aqueous solvent system; the use of aqueous systems may promote simultaneous deesterification of the cephalosporin compound when, for example, an anion exchange resin in the trifluoroacetate form is employed.

Compounds possessing a 3-substituent $$-CH_2Y$$

wherein Y is a hydroxy group may be prepared by the methods described in British Pat. No. 1,121,308 and Belgian Pat. No. 841,937.

Where Y is a halogen (i.e. chlorine, bromine or iodine) atom, ceph-3-em starting compounds may be prepared by halogenation of a β-acylamido-3-methylceph-3-em-4-carboxylic acid ester 1β-oxide followed by reduction of the 1β-oxide group later in the sequence as described in British Pat. No. 1,326,531. The corresponding ceph-2-em compounds may be prepared by the method of Dutch published Patent Application No. 6,902,013 by reaction of a 3-methylceph-2-em compound with N-bromosuccinimide to yield the corresponding 3-bromomethylceph-2-em compound.

Carbamoylation of 3-hydroxymethyl compounds may be effected by conventional methods. Thus, for example, a 3-hydroxymethyl cephalosporin may be reacted with an isocyanate of formula $R^e.NCO$ (wherein $R^e$ represents a labile substituent group or an alkyl group) to give a compound containing a 3-position substituent having the formula $-CH_2O.CONHR^e$ (wherein $R^e$ has the above defined meaning). Where $R^e$ is a labile substituent this substituent may if desired subsequently be cleaved, e.g. by hydrolysis, to form a 3-carbamoyloxymethyl group. Labile groups $R^e$ which are readily cleavable upon subsequent treatment include chlorosulphonyl and bromosulphonyl; halogenated lower alkanoyl groups such as dichloroacetyl and trichloroacetyl; and halogenated lower alkoxycarbonyl groups such as 2,2,2-trichloroethoxycarbonyl. These labile $R^e$ groups may generally be cleaved by acid or base catalysed hydrolysis (e.g. by base catalysed hydrolysis using sodium bicarbonate).

Another carbamoylating agent of use in the carbamoylation of 3-hydroxymethyl cephalosporins is cyanic acid, which is conveniently generated in situ from, for example, an alkali metal cyanate such as sodium cyanate, the reaction being facilitated by the presence of an acid, e.g. a strong organic acid such as trifluoroacetic acid. Cyanic acid effectively corresponds to a compound of formula $R^e.NCO$ wherein $R^e$ is hydrogen, and therefore converts 3-hydroxymethyl cephalosporin compounds directly to their 3-carbamoyloxymethyl analogues.

3-Hydroxymethyl cephalosporins for use in the above carbamoylation reactions may, for example, be prepared by the methods described in British Pat. No. 1,121,308 and Belgian Pat. Nos. 783,449 and 841,937.

Cephalosporin compounds possessing an acyloxymethyl group as 3-position substituent may, for example, be prepared from a cephalosporin compound having a $-CH_2X$ group (where $X = OH$ or the residue of an acid H X which has a pKa of not more that 4.0, preferably not more than 3.5, as measured in water at 25° C) at the 3-position. X may thus, for example, represent chlorine, bromine, iodine, formyloxy, an acetoxy group having at least one electron-withdrawing substituent on the α-carbon atom, or a nuclear substituted benzoyloxy group (the nuclear substituent being of the electron withdrawing type as described in British Pat. No. 1,241,657), and the nucleophilic displacement reaction to form the desired 3-position acyloxymethyl may be carried out as described in our aforesaid British Pat. No. 1,241,657. Alternatively, where X is hydroxy, a 3-acyloxymethyl cephalosporin may be obtained by acylation analogous with that described in British Pat. No. 1,141,293, i.e. by aralkylating the 4-carboxy group, acylating the 3-hydroxymethyl group of the protected compound and subsequently removing the aralkyl group.

Compounds having a vinyl or substituted vinyl group at the 3-position may be obtained by the method described in Belgian Pat. No. 761,897.

$\Delta^2$-Cephalosporin ester derivatives obtained in accordance with the process of the invention may be converted into the corresponding $\Delta^3$ derivative by, for example, treatment of the $\Delta^2$ ester with a base.

Ceph-2-em reaction products may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is $>S\rightarrow 0$ this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Where a compound of formula I is obtained as a mixture of isomers, the syn isomer may be obtained by, for example, conventional methods such as crystallisation or chromatography. Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-$d_6$ solutions of syn compounds of Formula I exhibit the doublet for the amide NH at a lower field than do similar solutions of the corresponding anti-isomers. These factors may be employed in monitoring reactions.

Acids (VI) may be obtained by reacting a glyoxylic acid of formula $$R.CO.COOH \qquad (VIII)$$

(where R has the above-defined meaning) or an ester thereof with a hydroxylamine derivative of formula

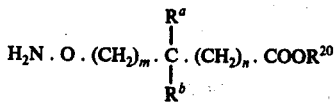

(IX)

(where $R^a$, $R^b$, $R^{20}$, $m$ and $n$ have the above-defined meanings). The resulting acid or ester may be separated into its syn and anti isomers by, for example, crystallisation, chromatography or distillation, whereafter ester derivatives may be hydrolysed to yield the corresponding acid.

Acids (VI) may also be prepared by etherification of an acid of formula

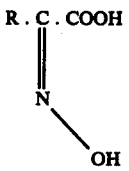

(X)

(where R has the above-defined meaning), e.g. by reaction with a compound of general formula

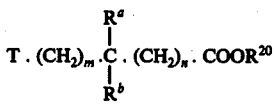

(XI)

(wherein $R^a$, $R^b$, $R^{20}$, $m$ and $n$ are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction.

Acids of formula VI and acylating agents derived therefrom (e.g. acyl halides such as the chloride) are novel and comprise a feature of the present invention.

Derivatives of the compounds of the invention in which the carboxy substituent of the 7β-acylamido side chain is substituted by a carboxyl blocking group are also new and comprise a feature of the invention. These monoester derivatives, which may be represented by the general formula

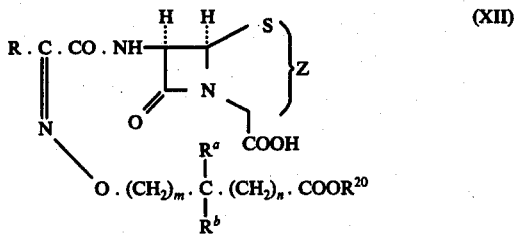

(XII)

(wherein R, $R^a$, $R^b$, Z, $m$ and $n$ are as hereinbefore defined and $R^{20}$ is a carboxyl blocking group such as t-butyl or diphenylmethyl), are of value as intermediates in the preparation of antibiotic compounds of general formula I. The compounds (XII) may themselves exhibit antibiotic activity, although generally at a very low level when compared to corresponding compounds (I).

Carboxyl blocking groups $R^{20}$ and, where appropriate, $R^{19}$ used in the preparation of compounds of formula I or in the preparation of necessary materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinylpyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. The tablets may be coated according to methods well known in the art. Oral liquid preparation may be in the form of, for example, aqueous or oily suspensions, solutions, emulsions, syrups or elixirs, or may be presented as a dry product for reconstitution with water or other suitable vehicle before use. Such liquid preparation may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following examples illustrate the invention. All temperatures are in °C. The structure of the products were verified by p.m.r. spectroscopy (Preparations and Examples) and i.r. spectroscopy (Examples only).

PREPARATION 1

2-t-Butoxycarbonylmethoxyimino-2-(fur-2-yl)acetic Acid (syn isomer)

The pH of a mixture of fur-2-ylglyoxylic acid (4.2g), t-butoxycarbonylmethoxyamine (4.5g) and water (50 ml) was adjusted to 5.0 with 2N sodium hydroxide solution. The resulting solution was stirred for 16 hours. The pH of the solution was increased to 7.0, and the solution was washed twice with ether. The aqueous solution was acidified to pH 1.8 under ether, and further extracted with ether. The combined ether extracts were washed (water, saturated brine), dried, and concentrated to give a solid (7.62g), which was crystallised from carbon tetrachloride to give the title compound (3.67g, 46%) m.p. 105.1°–106.2°; $\lambda_{max}$ (pH6 phosphate buffer) 277.5 nm ($\epsilon$ 16,300).

PREPARATION 2

2-t-Butoxycarbonylmethoxyimino-2-(thien-3-yl)acetic Acid (syn isomer)

Thien-3-ylglyoxylic acid and t-butoxycarbonylmethoxyamine were reacted as described in Preparation 1 to give the title compound, m.p. 102.6°–104.4° (from carbon tetrachloride); $\lambda_{max}$ (pH6 phosphate buffer) 258 nm ($\epsilon$ 13,700).

PREPARATION 3

2-RS-α-t-Butoxycarbonylbenzyloxyimino-2-(fur-2-yl) acetic Acid (syn isomer)

(a)(i) A mixture of N-hydroxyphthalimide (24.5g), anhydrous potassium carbonate (16.5g), t-butyl α-bromophenylacetate (41g) and dimethylsulphoxide (225 ml) was stirred for 18 hours and was then poured into water (1.2 liters). The precipitated solid was filtered off, washed well with water, dried, and crystallised from industrial methylated spirits to give N-[α-(t-butoxycarbonyl) benzyloxy] phthalimide (41g, 78%); m.p. 120.6°–121.5°.

(ii) To a solution of the above oxyphthalimide (40g) in dichloromethane (500 ml) was added 100% hydrazine hydrate (11.4 ml). A precipitate was formed immediately. The mixture was stirred for 1.5 hours, whereafter sufficient 5N ammonium hydroxide solution was added to dissolve the precipitate. The two layers were separated, and the aqueous layer was extracted once with methylene chloride. The combined organic extracts were washed (water, saturated brine), dried, and concentrated to give t-butyl α-(aminooxy)phenylacetate (25.0g, 98%) as colourless crystals, m.p. 48.2°–49.6°.

(b) Fur-2-ylglyoxylic acid and t-butyl α-(aminooxy) phenylacetate were reacted as described in Preparation 1 to yield the title compound in 42% yield, m.p. 97.9°–98.9° (from carbon tetrachloride); $\lambda_{max}$ (pH6 phosphate buffer) 278 nm ($\epsilon$ 18,400).

PREPARATION 4

2-t-Butoxycarbonylmethoxyimino-2-(thien-2-yl)acetic Acid (syn isomer)

To a stirred suspension of sodium hydride (60% dispersion in oil, 0.96g) in tetrahydrofuran (40 ml) was added 2-hydroxyimino-2-(thien-2-yl) acetic acid (syn isomer) (1.71g). The mixture was stirred for 30 minutes, after which time dimethylsulphoxide (25 ml) was added and stirring was continued for a further hour. t-Butyl chloroacetate (1.78g) was added to the mixture, which was stirred for 16 hours and was then poured into water (300 ml). After being washed twice with ether, the aqueous phase was acidified to pH 1.7. Extraction with ether and concentration of the washed (water, saturated brine) and dried extracts gave a solid (2.71 g) which was crystallised from carbon tetrachloride to give the title compound (0.952 g, 33%), m.p. 88.3°–91.3°; $\lambda_{max}$ (pH 6 phosphate buffer) 270.5 and 288.5 nm ($\epsilon$ 9,200 and 10,800).

PREPARATION 5

2-(2-t-Butoxycarbonylprop-2-yloxyimino)-2-(fur-2-yl)acetic Acid (syn isomer)

A solution of 2-(fur-2-yl)-2-hydroxyiminoacetic acid (syn isomer) (14.1g) in dimethyl sulphoxide (100ml) was added all at once to a magnetically stirred solution of potassium t-butoxide (22.4g) in dimethyl sulphoxide (400ml), the reaction mixture being maintained under an atmosphere of dry nitrogen. A gel was formed which, on stirring, became a finely divided, yellow solid. Stirring was continued for 1 hour, and then a solution of t-butyl 2-bromo-2-methylpropionate (24.0g) in dimethyl sulphoxide (50ml) was added over 1 hour to the reaction mixture at room temperature. After addition was complete, the resulting solution was stirred for a further hour. The reaction was poured into ice-water (1.5 liters) and acidified under ether (500ml) to pH 1.8 with concentrated hydrochloric acid. The two layers were separated, and the aqueous layer was extracted with more ether. The combined ether extracts were washed once with water, then extracted with aqueous sodium bicarbonate solution. The combined alkaline extracts were acidified under ether to pH 1.8 with concentrated hydrochloride acid, and the acid solution was extracted further with ether. The combined ether extracts were washed (water, saturated brine), dried, and concentrated to a yellow oil, which crystallised under high vacuum (22.41g, 83%), $\lambda_{max}$(EtOH) 272.5nm ($\epsilon$ 15,400).

The above solid (22.4g) was crystallised from carbon tetrachloride (25ml) to give the title compound (16.42g, 61%), m.p. 72.5°–74.2° (73.0°).

PREPARATIONS 6–19

Method A

The dipotassium salt of 2-(fur-2-yl)-2-hydroxyiminoacetic acid (syn isomer) was generated under an atmosphere of dry nitrogen and alkylated with the appropriate halo-t-butyl ester as described in Preparation 5. The products were isolated by pouring into water, acidifying, and extracting in the conventional manner.

Method B

As method A but using a halo-diphenylmethyl ester.
The half esters prepared by these methods are listed in Table 1.

TABLE 1

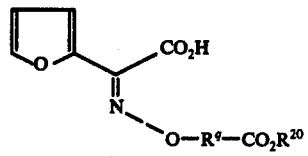

| Preparation No. | $R^q$ | $R^{20}$ | Method | m.p. °C | $\lambda_{max}$nm (Solvent) | c | $\tau$ values for $d_6$-DMSO $R^q$ | $R^{20}$ |
|---|---|---|---|---|---|---|---|---|
| 6 | \CHCH₃/ | —C(CH₃)₃ | A | 69.8–73.4° | 277(pH6 buffer) | 15,500 | 5.31;8.56 | 8.58 |
| 7 | —CH₂— | " | A | 107° | 271(EtOH) | 13,700 | 5.32 | 8.56 |
| 8 | ⋈ (cyclopropyl) | " | A | 106.8–107.3° | 277.5(pH6 buffer) | 15,100 | 8.03;8.30 | 8.63 |
| 9 | \CH(CH₂)₃CH₃/ | —CHPh₂ | B | 102–104° | 275(EtOH) | 12,700 | 5.1;8.16; 8.7;9.18 | 3.07(CH) |
| 10 | \CHCH₂CH₃/ | " | B | — | 271.5 (EtOH) | 14,100 | 5.13;8.11 9.07 | 3.09(CH) |
| 11 | \C(C₂H₅)₂/ | " | B | — | 269(EtOH) | 13,200 | 8.08;9.22 | 3.10(CH) |
| | | | | | | | $\tau$ values (solvent) | |
| 12 | \CH(CH₂)₂CH₃/ | —CHPh₂ | B | 116–117° | 270(EtOH) | 14,750 | 5.10;7.9–8.9; 9.1($d_6$-DMSO) | 3.08(CH) |
| 13 | \CH—C₆H₁₁/ | —CHPh₂ | B | — | 270(EtOH) | 13,400 | 5.32;7.8–9.2 ($d_6$-DMSO) | 3.07(CH) |
| 14 | \CH—CH(CH₃)₂/ | —CHPh₂ | B | — | 270.5 266.5 (EtOH) | 13,700 13,250 | 5.14;7.68;8.95 9.15(CDCl₃) | 3.05(CH) |
| 15 | \CH—CH₂CH=CH₂/ | —C(CH₃)₃ | A | 77.0–80.3° | 276.5 (pH6 buffer) | 17,500 | 4.26;4.86;4.91 5.38;7.44 ($d_6$-DMSO) | 8.60 |
| 16 | ⬡ (cyclohexyl) | " | A | 91.5° | 276.5 (pH6 buffer) | 16,700 | 8.12;8.50 ($d_6$-DMSO) | 8.57 |
| 17 | \C(CH₃)(CO₂C(CH₃)₃)/ | " | A | 91.5–93.8° | 276(pH6 buffer) | 15,800 | 8.39;8.56 ($d_6$-DMSO) | 8.56 |
| | | | | | | | $\tau$ values $d_6$-DMSO | |
| 18 | ⬨ (cyclobutyl) | —C(CH₃)₃ | A | 113–114° | 278(pH6 buffer) | 17,200 | 7.4–8.3 | 8.59 |
| 19 | \C(CH₃)(CO₂C₂H₅)/ | " | A | + | — | — | 5.76;8.74;8.33 (CH₃) | 8.54 |

TABLE 1-continued

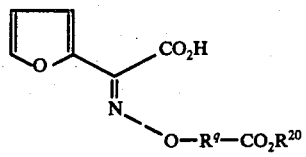

| | | | | | | |
|---|---|---|---|---|---|---|
| 20 | —CH$_2$< | —CHPh$_2$ | B | — | — | — | 5.49;8.6–8.9 | 3.15(CH) |

*Denotes (RS)-isomers
+N-benzyl-2-Phenylethylammonium salt mp. 129°

PREPARATION 21

2-(2-t-Butoxycarbonylprop-2-yloxyimino)-2-(thien-2-yl) acetic Acid (syn isomer)

The title compound was prepared from 2-hydroxyimino-2-(thien-2-yl)acetic acid (syn isomer) and t-butyl 2-bromo-2-methylpropionate, in a similar manner to that described for Preparation 5, in 78% yield as a colourless oil, and was characterised as the N-benzyl-2-phenylethylammonium salt, m.p. 201.3°–201.9° (from ethanol).

PREPARATION 22

2-(2-t-Butoxycarbonylethoxyimino)-2-(fur-2-yl)acetic Acid (syn isomer)

To a mixture of methyl acetohydroximic acid [CH$_3$.C(:NOH).OCH$_3$] (8.9g) and t-butyl acrylate (12.8g) was added a solution of potassium t-butoxide (0.1g) in t-butanol (1ml). The mixture was kept at 0° for 65 hours, then washed with water, dried, and distilled, to give 2-t-butoxycarbonylethyl methyl acetohydroximate (2.37g, 11%), b.p. 85°–87°/1.2mm Hg.

To a solution of fur-2-ylglyoxylic acid (1.26g) in water (50ml) was added 2-t-butoxycarbonylethyl methyl acetohydroximate (2.15g) and sufficient methanol to give a homogeneous mixture, which was stirred for 30 minutes at pH 1.5. The pH was adjusted to 4.5 with 2N sodium hydroxide solution, and the mixture was stirred for a further 16 hours, when reaction was almost complete. Methanol was removed under reduced pressure, the pH of the residue was raised to 7.0, and the aqueous mixture was washed twice with ether. The aqueous phase was acidified in the presence of dichloromethane to pH 1.7, and the phases were separated. The aqueous phase was extracted twice more with dichloromethane. The combined dichloromethane extracts were washed with water, dried, and concentrated to give a fawn solid (1.53g) (mixture of syn and anti isomers, 85:15) which was crystallised from carbon tetrachloride to give the title compound (0.975g, 34%), m.p. 74.7°–77.2°; $\lambda_{max}$ (pH6 buffer) 277nm ($\epsilon$ 16,500).

PREPARATION 23 t-Butyl 1-Bromocyclopentanecarboxylate

To a mixture of 1-bromocyclopentanecarboxylic acid (36.99g) and anhydrous ether (35ml) in a 500ml pressure bottle, containing a magnetic stirrer-bar, was added concentrated sulphuric acid (3.5ml), followed by precondensed isobutene (150ml). The bottle was sealed, and stirred at ambient temperature for 20 hours. The bottle was then opened. excess isobutene was evaporated, and the residue in ether was washed with aqueous sodium bicarbonate solution and water, dried, and concentrated. The residue was distilled under reduced pressure to give the title ester (b.p. 66°–74°/0.5–2.0mm) (33.6g, 70%); $\lambda_{max}$(CHBr$_3$) 1702cm$^{-1}$; $\tau$ (CDCl$_3$) 7.78, 8.20 (cyclopentane protons) and 8.54 (C(CH$_3$)$_3$).

PREPARATION 24

Diphenylmethyl α-bromohexanoate

α-Bromohexanoic acid (1.95g) in light petroleum spirit (25ml, b.p. 40°–60°) was treated with a stock solution of diphenyldiazomethane in petroleum spirit (b.p. 40°–60°) (ca. 3.8 mmole/10ml) dropwise with stirring until a faint violet colour persisted. The mixture was stirred for 2 hours at room temperature, whereupon the solvent was removed in vacuo. The resulting oil in ethyl acetate was washed with a saturated aqueous solution of sodium bicarbonate then with water and dried. Removal of the solvent gave the title ester (3.0g, 90%), $\lambda_{max}$ (EtOH) 252, 258, 263.5, 267.5 and 276 nm ($\epsilon$ 1650, 1600, 1350, 1150 and 850).

PREPARATION 25–34

α-Halo Substituted Carboxylic Acid Esters

Method A

The appropriate α-halo carboxylic acid was treated with isobutene and concentrated sulphuric acid in a pressure bottle at room temperature for 10–40 hours by the method described in Preparation 23 to give the t-butyl esters listed in Table 2.

Method B

The appropriate α-halo carboxylic acid in a solvent (e.g. ether, petroleum, ethyl acetate) was treated with a solution of diphenyldiazomethane until a faint permanent colour was obtained. The ester was washed with alkali in the manner described in Preparation 24 to give the diphenylmethyl esters listed in Table 2.

TABLE 2

X—R$^q$—CO$_2$R$^{20}$

| Preparation No. | X | R$^q$ | R$^{20}$ | Method | Ester $\nu_{max}$cm$^{-1}$ (CHBr$_3$) | $\tau$ values (solvent) R$^q$ | R$^{20}$ |
|---|---|---|---|---|---|---|---|
| 25 | Cl | —CH$_2$— | —C(CH$_3$)$_3$ | A | 1735 | 4.06(CDCl$_3$) | 8.53 |

TABLE 2-continued

| | | | | | τ values (CHCl₃) | |
|---|---|---|---|---|---|---|
| 26 | Br\C(CH₃)₂/ | " | A | 1716 | 5.74;8.22(CDCl₃) | 8.51 |
| 27 | Br\CHCH₂CH₃*/ | —CHPh₂ | B | 1737 | 5.29;7.97;9.07 (d₆-DMSO) | 3.10(CH) |
| 28 | Br\C(C₂H₅)(C₂H₅)/ | " | B | 1729 | 7.81;9.10(d₆-DMSO) | 3.06(CH) |
| 29 | Br\CH(CH₂)₂CH₃*/ | " | B | 1730 | 5.24;7.7–8.9;9.12 (d₆-DMSO) | 3.09(CH) |
| 30 | Br\CH—⟨⟩*/ | " | B | 1725,1245 | 5.45,7.8–9.3(d₆-DMSO) | 3.04(CH) |
| 31 | Br\CHCH(CH₃)₂*/ | " | B | 1738 | 5.40;7.79;9.0;9.08 (d₆-DMSO) | 3.10(CH) |

| | | | | | τ values (CHCl₃) | |
|---|---|---|---|---|---|---|
| 32 | Br⟨hexagon⟩ | —C(CH₃)₃ | A | 1710 | 7.9;8.0–8.9 | 8.51 |
| 33 | Br⟨rhombus⟩ | " | A | 1714 | 6.9–7.6;7.7–8.3 | 8.52 |
| 34 | Br—CH₂⟨triangle⟩ | —CHPh₂ | B | — | 6.29;8.2–9.1 | 3.08(CH) |

*Denotes (RS)-isomers

PREPARATION 35

Di-t-butyl 2-Bromo-2-methylmalonate

To a stirred suspension of sodium hydride (1.7g, 80% dispersion in oil) in tetrahydrofuran (60 ml) under an atmosphere of nitrogen was added di-t-butyl methylmalonate (11.52g). The mixture was stirred at 60°–70° for 1.5 hours to give a clear solution. This solution was cooled to −25°, and to it was rapidly added a solution of bromine (2.6 ml) in dichloromethane (30ml). The solution was allowed to warm to ambient temperature, then concentrated. The residue in ether was washed with water, dried, and fractionally distilled under reduced pressure to give the title compound b.p. 78°–86°/1.0 mm Hg, (7.56g, 49%); $v_{max}$(CHBr₃) 1730cm⁻¹ (CO₂Buᵗ); τ (CDCl₃) values include 8.05 (s, C(CH₃)₃) and 8.53 (2s, CH₃ and C(CH₃)₃).

PREPARATION 36 t-Butyl Ethyl 2-Bromo-2-methylmalonate

The title compound was prepared in a similar manner to that used for the dibutyl ester in Preparation 35, in 83% yield, b.p. 64°–68°/0.03mm Hg.

PREPARATION 37

1-Bromomethylcyclopropane-1-carboxylic Acid

The bromination of cyclobutane carboxylic acid led to the corresponding bromoacid together with the title acid (ca. 15% yield), m.p. 83°–84° (petroleum spriit b.p. 60°–80°); τ (d₆-DMSO) values 6.25, 8.65 and 8.90.

EXAMPLE 1

(a)
(6R,7R)-3-Acetoxymethyl-7-[2-t-butoxycarbonylmethoxyimino-2-(fur-2-yl)acetamido] ceph-3-em-4-carboxylic acid (syn isomer)

Oxalyl chloride (0.45 ml) was added at 5° to a stirred solution of 2-t-butoxycarbonylmethoxyimino-2-(fur-2-yl) acetic acid (syn isomer) (1.35 g) in dry dichloromethane (50 ml) containing triethylamine (0.7ml) and dimethylformamide (1 drop). The solution was stirred at 5° for 1 hour and was then evaporated to dryness at 5°. The residue was suspended in acetone (50ml) and was added over 30 minutes to a stirred, ice-cooled solution of (6R,7R)-3-acetoxymethyl-7-aminoceph-3-em-4-carboxylic acid (1.36g) in water (100ml) and acetone (50ml) containing sodium bicarbonate (1.0g). The reaction mixture was stirred for 1 hour, whereafter the acetone was evaporated under reduced pressure. The residue was acidified to pH 1.8, and this mixture was extracted with ether. The combined extracts were washed (water, saturated brine), dried, and evaporated to give the title compound (2.52g, 96%) as a pale yellow foam, $[\alpha]_D$ + 28.5° (c. 0.96, DMSO); $\lambda_{max}$ (pH6 phosphate buffer) 276.5nm (ε 17,900).

(b)
(6R,7R)-3-Acetoxymethyl-7-[2-carboxymethoxyimino-2-(fur-2-yl)-acetamido]ceph-3-em-4-carboxylic Acid, Disodium Salt (syn isomer)

A solution of (6R,7R)-3-acetoxymethyl-7-[2-t-butoxycarbonylmethoxyimino-2-(fur-2-yl)acetamido]ceph-3-em-4-carboxylic acid (syn isomer) (1.422g) and anisole (0.25ml) in trifluoroacetic acid (5ml) was kept at ambient temperature for 5 minutes. The mixture was concentrated at reduced pressure, ethyl acetate (10ml) was added, and the mixture was re-evaporated. The residue was distributed between ether and sodium bicarbonate solution. The ether layer was extracted further with sodium bicarbonate solution and the combined alkaline extracts were acidified to pH 1.8 under ether. The acid mixture was extracted with ether, and the combined ether extracts were washed (water, saturated brine), dried, and evaporated to give the dicarboxylic acid corresponding to the title compound (942 mg, 74%), τ (d$_6$ - DMSO) values include 0.24 (d, J 8Hz, N$\underline{H}$), 4.13 (dd, 7-$\underline{H}$), and 5.31 (s, C$\underline{H}_2$CO$_2$H).

This di-acid (900mg) in acetone (9ml) was neutralised with a solution of sodium 2-ethylhexanoate (700mg) in acetone (5ml). The mixture was stirred for 10 minutes, then the precipitated solid was filtered off, washed with a little acetone, and dried to give the title compound (807mg, 60%), [α]$_D$ + 15° (c 1.08, DMSO); $\nu_{max}$(Nujol) 1766 cm$^{-1}$ (β-lactam).

EXAMPLES 2-26

GeneraL Procedure for the Preparation of (6R,7R)-7-(2-Aryl-2-carboxy-R$^q$-oxyiminoacetamido)-3-(substituted) ceph-3-cm-4-carboxylic Acids (syn-isomers) and/or their Salts Method A Following the procedure described in Example 1, a solution of the appropriate 2-aryl-2-t-butoxycarbonyl-R$^q$-oxyiminoacetic acid (syn-isomer) (1 equiv) in methylene chloride optionally containing a few drops of N,N-dimethylformamide and triethylamine (1 equiv) was treated with oxalyl chloride (1 equiv) at 0°-5° for ca. 1 hour. The mixture was then evaporated to dryness. The residue was suspended or dissolved in acetone and added to a stirred, ice-cold solution of (6R,7R)-3-acetoxymethyl-7-aminoceph-3-em-4-carboxylic acid (1-1.2 equiv) in water or a mixture of acetone and water containing sodium hydrogen carbonate (2-2.5 equiv). The reaction mixture was stirred for 0.5-2.5 hours, allowing the temperature to rise to room temperature, whereafter the acetone was removed under reduced pressure. The pH was adjusted to 1.5-2.0 and the product extracted into ethyl acetate (alternatively ether or methylene chloride may be used). The organic layer was washed with water and/or saturated brine, dried and evaporated to give the corresponding (6R,7R)-3-acetoxymethyl-7-(2-aryl-2-t-butoxycarbonyl-R$^q$-oxyiminoacetamido)ceph-3-em-4-carboxylic acid (syn-isomer) which was characterised by optical rotation and/or by spectroscopy.

The t-butyl esters were deprotected by treating with trifluoracetic acid containing anisole at room temperature for at least 5 minutes. The reaction mixture was evaporated in vacuo and the product isolated by trituration or by distributing between ethyl acetate (or ether) and an aqueous solution of sodium hydrogen carbonate, separating the aqueous extracts, acidifying these extracts under ethyl acetate and isolating the title dicarboxylic acid in the usual way. The products are listed in Table 3.

Method B

As Method A except that the appropriate 2-aryl-2-diphenylmethoxycarbonyl-R$^q$-oxyiminoacetic acid (syn-isomer) was used in place of the t-butyl ester. The products are listed in Table 3.

Method C

As Method A or B except that the dicarboxylic acid was converted into its disodium salt by treating a solution of the acid in acetone with a solution of sodium 2-ethylhexanoate in acetone. The precipitated disodium salt was washed and dried. The products are listed in Table 3.

Method D

As Method A except that a (6R,7R)-3(substituted methyl)-7-aminoceph-3-em-4-carboxylic acid or salt thereof was used in place of (6R,7R)-3-acetoxymethyl-7-aminoceph-3-em-4-carboxylic acid. The products are listed in Table 4.

TABLE 3

| Ex. No. | R$^p$ | R$^q$ | Salt | Method | [α]$_D$ (DMSO) | λ$_{max}$, nm (pH 6 buffer) | ε | β-lactam $\nu_{mx}$ cm$^{-1}$ (Nujol) | τ values* for d$_6$-DMSO at 100 MHz | | |
|---|---|---|---|---|---|---|---|---|---|---|---|
| | | | | | | | | | x | y | R$^g$ |
| 2 | (thiophene) | —CH$_2$— | di-sodium | A,C | +26.5° | 263 / 292 | 14,900 / 10,200 | 1762 | 0.15 | 4.10 | 5.32 |
| 3 | (thiophene) | —CH$_2$— | — | A | +35° | 262 | 19,700 | 1798 | 0.26 | 4.05 | 5.21 |
| 4 | (furan) | >CHPh** | — | A | +48° | 277.5 | 18,700 | 1778 | 0.13; 0.20 | 4.08; 4.16 | 4.28; 4.32(CH) 2.3 – 2.6(Ph) |
| 5 | (furan) | >CHCH$_3$** | di-sodium | A,C | +63° | 275 | 16,800 | 1764 | 0.29 | 4.10 | 5.27(CH) 8.54(CH$_3$) |

TABLE 3-continued
| | R' | R^a | | | [α] | λ_max nm (EtOH) | ε | ν (cm⁻¹) | Rf | | |
|---|---|---|---|---|---|---|---|---|---|---|---|
| 6 |  | >C(CH₃)₂ | di-sodium | A,C | +95° | 274 | 16,800 | 1768 | 0.32 | 4.05 | 8.47 |
| 7 | 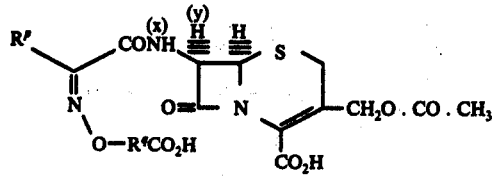 |  | di-sodium | A,C | +62° | 276 | 16,800 | 1756 | 0.38 | 4.10 | 7.90 and 8.28 |
| 8 |  | >CHCH₂CH=CH₂** | di-sodium | A,C | +40° | 276 | 15,400 | 1760 | 0.29 | −4.15 | 4.1,~4.8, 5,34 7.38 |
| 9 |  |  | di-sodium | A,C | +76.5° | 275 | 15,500 | 1756 | 0.38 | 4.13 | 8.20, 8.50 |
| 10 |  | >C(CO₂H)(CH₃) | — | A | +43° | 274.5 | 10,100 | 1760 | 0.37 | 4.16 | 8.36 |
| 11 |  |  | — | A,B | +28° | 274 | 14,600 | 1780 | 0.31 | 4.09 | 7.56, 8.08 |
| 12 |  | >C(CO₂Et)(CH₃)** | — | A | +21° | 275.5 | 17,200 | 1790 | 0.33 | 4.16 | 5.80, 8.33, 8.80 |
| 13 |  | >CH(CH₂)₃CH₃** | — | B | +45° | 274 | 19,150 | 1771 | 0.31 | 4.11 | 5.40; 8.2; 8.6; 9.1 |
| 14 |  | >CHCH₂CH₃** | — | B | +57° | 274 | 18,000 | 1776 | 0.35 | 4.10 4.13 | 5.45; 5.50 8.12; 9.01 |
| 15 |  | >C(C₂H₅)₂ | — | B | +44° | 272.5 | 17,000 | 1773 | 0.41 | 4.16 | 8.1; 9.2 |
| 16 |  | >CH(CH₂)₂CH₃** | — | B | +53° | 273 | 16,900 | 1780 | 0.37 | 4.10 4.12 | 5.40; 5.42 8.2; 8.5; 9.1 |
| 17 |  | >CH—** | — | B | +41° | 273 | 18,250 | 1782 | 0.4 | 4.18 | 5.65; 8.0 – 9.2 |
| 18 |  | >CHCH(CH₃)₂** | — | B | +69° | 273 | 18,100 | 1781 | 0.38 | 4.14 | 5.61; 5.69 7.85; 9.0 |
| 19 | 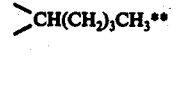 | >C(CH₃)₂ | — | A | +62.5° | 262 | 13,900 | 1784 | 0.37 | 4.10 | 8.51 |
| 20 |  | —CH₂CH₂— | — | A | +31° | 276.5 | 15,800 | 1784 | 0.28 | 4.19 | 5.68; 7.34 |
| 21 |  | —CH₂ | — | B | +43° | 276 | 17,250 | 1784 | 0.33 | 4.17 | 5.68; 8.7–9.0 |
**Denotes (RS)-isomers
*Values for free acids

TABLE 4

[Structure: R^p-C(=N-O-R^q)-CONH-CH(x)-CH(y)-... cephem core with CH_2Y and CO_2H]

| Ex. No. | R^p | R^q | Y | Salt | Method | $[\alpha]_D$ (solvent) | $\lambda_{max}$ nm (pH6 buffer) | $\epsilon$ | β-lactam $\nu_{max}$ cm$^{-1}$ (Nujol) | τ' values for d$_6$-DMSO at 100 MHz x | y | R^q |
|---|---|---|---|---|---|---|---|---|---|---|---|---|
| 22 | furyl | —CH$_2$— | —N$_3$ | — | D | +35° (dioxan) | 275 | 15,200 | 1770 | 0.14 | 4.10 | 5.31 |
| 23 | furyl | cyclopentyl | —OCONHCH$_3$ | — | D | +41.2° (DMSO) | 277 | 17,850 | 1780 | 0.48 | 4.18 | 7.95; 8.3 |
| 24 | thienyl | —CH$_2$— | —OCONH$_2$ | di-sodium | D | +47.5° (DMSO) | 264 | 13,900 | 1770 | 0.25 | 4.13 | 5.33 |
| 25 | furyl | cyclobutyl | —OCONH$_2$ | — | D | +26° (DMSO) | 277.5 | 15,100 | 1788 | 0.34 | 4.12 | 7.56; 8.10 |
| 26 | furyl | >C(CH$_3$)$_2$ | —OCONH$_2$ | di-sodium | D | +44° (H$_2$O) | 274.5 | 14,950 | 1773 | 0.44 | 4.15 | 8.52 |

EXAMPLE 27

(6R,7R)-7-[2-Carboxymethoxyimino-2-(fur-2-yl)-acetamido]-3-(1-methyltetrazol-5-ylthiomethyl)ceph-3-em-4-carboxylic acid (syn isomer)

A solution of 2-t-butoxycarbonylmethoxyimino-2-(fur-2-yl)acetic acid (syn isomer) (0.97g) in methylene chloride (20ml) was added dropwise at room temperature over 15 minutes to a stirred solution of diphenylmethyl (6R,7R)-7-amino-3-(1-methyltetrazol-5-ylthiomethyl)ceph-3-em-4-carboxylate (1.484 g) and dicyclohexylcarbodiimide (0.743g) in methylene chloride (45 ml). After stirring for a further 2 hours the solvent was removed by evaporation, and the residue was stirred for 5 minutes with ethyl acetate (50 ml) and filtered. The filtrate was washed with saturated sodium bicarbonate solution, diluted with an equal volume of water and then with brine (25 ml of each), dried and evaporated to a foam (2.5 g) which was dissolved in benzene and purified by chromatography on Kieselgel (70 g). Elution with benzene : ethyl acetate (10:1), combination of appropriate fractions and evaporation to dryness gave a foam (2.05g) which was dissolved in ethyl acetate and run into light petroleum to give diphenylmethyl (6R,7R)-7-[2-t-butoxycarbonylmethoxyimino-2-(fur-2-yl)-acetamido]-3-(1-methyltetrazol-5-ylthiomethyl)ceph-3-em-4-carboxylate (syn isomer) (2.02 g, 90%) as a white amorphous solid, $[\alpha]_D^{23}$ − 102° (c 0.99, CHCl$_3$); $\lambda_{max}$ (EtOH) 278 nm ($\epsilon$ 19,800).

A solution of this diester (1.93 g) in a mixture of trifluoroacetic acid (7.7 ml) and anisole (1.9 ml) was kept at 0° for 10 minutes and then added to a mixture of saturated sodium bicarbonate and water (1:3, 850 ml). After stirring for 10 minutes the mixture was washed with ethyl acetate, covered with more ethyl acetate (200 ml) and acidified to pH 2 with concentrated hydrochloric acid. The organic phase was separated, washed with water and brine, dried and evaporated to a foam (1.54 g). Thin layer chromatography suggested that deprotection was incomplete and the product was retreated with trifluoroacetic acid (4.3 ml) and anisole (1.1 ml) at 20° for 15 minutes, whereafter the product was isolated as a foam (1.3 g) as described above. This foam in ethyl acetate was run into light petroleum to give the title dicarboxylic acid (0.8 g, 59%) as a white amorphous solid, $[\alpha]_D^{23}$ − 99° (c 1.05, acetone); $\lambda_{max}$ (0.1M-pH 6 phosphate buffer) 277 nm ($\epsilon$ 21,900); $\nu_{max}$ (Nujol) 1780 cm$^{-1}$; τ (d$_6$-DMSO) values include 0.19 (d,NH), 4.14 (dd, 7-H), 5.30 (s, CH$_2$CO$_2$H).

EXAMPLE 28

(6R,7R)-3-Carbamoyloxymethyl-7-[2-carboxymethoxyimino-2-(fur-2-yl)acetamido]ceph-3-em-4-carboxylic acid (syn isomer)

Diphenylmethyl (6R,7R)-7-amino-3-carbamoyloxymethylceph-3-em-4-carboxylate toluene-p-sulphonic acid salt (2.08 g) was dissolved in a mixture of ethyl acetate (60 ml) and saturated aqueous sodium bicarbonate (60 ml). The ethyl acetate layer was separated, washed with water, dried, and evaporated to a foam.

2-t-Butoxycarbonylmethoxyimino-2-(fur-2-yl)acetic acid (syn isomer) (1.0 g) and dicyclohexylcarbodiimide (0.76 g) dissolved in a small volume of anhydrous dichloromethane were added to a solution of the above amine dissolved in anhydrous dichloromethane (20 ml). The reaction mixture was stirred at 3° for 35 minutes, during which time N,N'-dicyclohexylurea crystallised out. This was filtered off and the filtrate was evaporated to an oil which solidified on trituration with diisopropyl ether. The solid product was dissolved in ethanol and decolourised with charcoal. Evaporation of the solution gave diphenylmethyl (6R,7R)- 3-carbamoyloxymethyl-7-[2-t-butoxycarbonylmethoxyimino-2-(fur-2-yl)acetamido]ceph-3-em-4-carboxylate (syn isomer) (2.08 g, 86%); m.p. 97°-98°; $[\alpha]_D$ + 5.5° (c 1.00, DMSO); $\lambda_{max}$ (EtOH) 276.5 mm ($\epsilon$ 17,250).

Trifluoroacetic acid (6 ml) was added to a slurry of the above diester (2.08 g) in anisole (6 ml) and the reaction mixture was stirred at 20° for 25 minutes. The solution was poured into a mixture of ethyl acetate and aqueous sodium bicarbonate solution, the aqueous layer was separated and washed with ethyl acetate. Ethyl acetate (100 ml) and 2N-hydrochloric acid were added to reduce the pH to 2. The organic layer was then separated, washed with water, dried, and evaporated to a yellow oil. P.m.r. indicated this product to be (6R,7R)-3-carbamoyloxymethyl-7-[2-t-butoxycarbonylmethoxyimino-2-(fur-2-yl)acetamido]ceph-3-em-4-carboxylic acid (syn isomer).

This acid was treated with anisole (4 ml) and trifluoroacetic acid (4 ml) at 20° for 30 minutes and the reaction mixture was partitioned between ethyl acetate and aqueous sodium bicarbonate solution. The aqueous layer was washed with ethyl acetate and acidified to pH 2 with 2N-hydrochloric acid under ethyl acetate. Evaporation of the ethyl acetate layer gave a solid which was purified by precipitation from ethyl acetate with diisopropyl ether and filtered off to give the title dicarboxylic acid (620 mg, 44%); m.p. 159°–161°; $[\alpha]_D^{21} + 35°$ (c 1.0, DMSO); $\lambda_{max}$ (pH 6 phosphate buffer) 275 nm ($\epsilon$ 15,400); $\nu_{max}$ (Nujol) 1778 cm$^{-1}$, $\tau$ (d$_6$-DMSO) values include 0.20 (d,NH) 4.15 (dd, 7-H) 5.32(s, C(CH$_3$)$_2$).

EXAMPLES 29–39

General Procedure for the Preparation of (6R,7R)-7-[2-carboxy-R$^q$-oxyimino-2-(fur-2-yl)acetamido]-3-(substituted)ceph-3-em-4-carboxylic acids (syn isomers) using Dicyclohexylcarbodiimide (i) To a solution of a diphenylmethyl (6R,7R)-7-amino-3-(substituted)ceph-3-em-4-carboxylate (1 equiv) and dicyclohexylcarbodiimide (1–1.3 equiv) in dry methylene chloride was added at 0°–25° a solution of the appropriate 2-t-butoxycarbonyl-R$^q$-oxyimino-2-(fur-2-yl)acetic acid (syn isomer) (1–1.15 equiv) in dry methylene chloride. After stirring for 0.5–5.0 hours the dicyclohexylurea was removed by filtration and the filtrate was evaporated. The residue in ethyl acetate or methylene chloride was washed successively with aqueous sodium bicarbonate, water and brine, dried and evaporated. The diester was purified by chromatography on silica or, after decolourisation with charcoal, by trituration or crystallisation. The product was characterised by its p.m.r. spectrum and by thin layer chromatography.

Where the 7-amino starting material was available as an acid addition salt the free base was liberated by shaking with a mixture of ethyl acetate (or methylene chloride) and an excess of an aqueous solution of sodium bicarbonate. After washing with water and brine the organic layer was evaporated to dryness and the free amine used as described above.

(ii) Method A

The intermediate diesters so derived were deprotected by dissolving in a mixture of trifluoracetic acid (3–10 ml/1 g of diester) and anisole (0.8–12 ml/1 g of diester) and left at between 0° and room temperature for between 5 minutes and 2.5 hours. The mixture was concentrated under reduced pressure and added to a mixture of ethyl acetate or ether and excess aqueous sodium bicarbonate, and the aqueous layer was washed with ethyl acetate. The aqueous phase was covered with ethyl acetate and acidified to pH 1–2 with hydrochloric acid. The organic layer was washed, dried and evaporated to give the required dicarboxylic acid.

(ii) Method B

In some cases where treatment with trifluoroacetic acid was insufficient to complete deprotection the intermediate monoester (usualy the t-butoxycarbonyl group was cleaved more slowly than the diphenylmethoxycarbonyl group) was retreated with trifluoracetic acid and anisole and the diacid isolated as described above.

(iii) Method C

The 3-carboxyvinyl derivative described in Example 35 was prepared from a 7-amino derivative in which both carboxy groups were protected as the diphenylmethyl ester. The resulting triester was deprotected as in Method B to provide the required tricarboxylic acid.

The properties of the reaction products are listed in Table 5.

TABLE 5

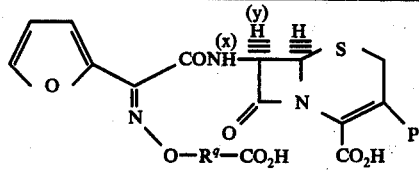

| Ex. No. | R$^q$ | P | Method | $[\alpha]_D$ (solvent) | $\lambda_{max}$, nm (solvent) | $\epsilon$ | β-lactam $\nu_{max}$, cm$^{-1}$ (Nujol) | τ values for d$_6$-DMSO at 100 MHz | | |
|---|---|---|---|---|---|---|---|---|---|---|
| | | | | | | | | x | y | R$^q$ |
| 29 | >C(CH$_3$)$_2$ | —CH$_2$S—[tetrazole N-CH$_3$] | B | −12° (H$_2$O) | 278 (pH 6 buffer) | 20,050 | 1781 | 0.33 | 4.1 | 8.51 |
| 30 | >C(CH$_3$)$_2$ | —CH$_2$OCONH$_2$ | B | +62° (EtOH) | 275 (pH 6 buffer) | 14,850 | 1775 | 0.24 | 4.14 | 8.52 |
| 31 | —CH$_2$— | —CH═CHCO$_2$CH$_3$ (trans) | B | −103° (aq.NaHCO$_3$) | 295 (pH 6 buffer) | 26,200 | 1775 | 0.20 | 4.08 | 5.32 |
| 32 | >C(CH$_3$)$_2$ | —CH$_2$S—[thiadiazole-CH$_3$] | A | −48° (DMSO) | 278 (pH 6 buffer) | 21,800 | 1780 | 0.38 | 4.1 | 8.49; 8.57 |

TABLE 5-continued

| Ex. No. | R$^q$ | P | Method | $[\alpha]_D$ (solvent) | $\lambda_{max}$, nm (solvent) | $\epsilon$ | β-lactam $\nu_{max}$ cm$^{-1}$ (Nujol) | τ values for d$_6$-DMSO at 100 MHz | | |
|---|---|---|---|---|---|---|---|---|---|---|
| | | | | | | | | x | y | R$^q$ |
| 33 | (cyclopentylidene) | CH$_2$S—(benzothiazolyl) | A | −89° (DMSO) | 221 283 (pH 6 buffer) | 23,900 21,550 | 1772 | 0.42 | 4.10 | 7.9; 8.3 |
| 34 | " | —CH=CHCO$_2$C$_2$H$_5$ (trans) | B | −8° (aq.NaHCO$_3$) | 295 (pH 6 buffer) | 26,200 | 1780 | 0.38 | 4.09 | 7.9; 8.3 |
| 35 | " | —CH=CHCO$_2$H (trans) | C | −15° (aq.NaHCO$_3$) | 294.5 (pH 6 buffer) | 31,200 | 1779 | 0.38 | 4.07 | 7.9; 8.3 |
| 36 | " | —CH$_2$S—(1-methyltetrazolyl) | A | −71° (CHCl$_3$) | 279 (pH 6 buffer) | 22,000 | 1780 | 0.42 | 4.15 | 7.9; 8.28 |
| 37 | " | —CH$_2$OCONH$_2$ | A | +52° (EtOH) | 274.5 (pH 6 buffer) | 15,700 | 1778 | 0.45 | 4.14 | 7.9; 8.25 |
| 38 | " | —CH=CHCO$_2$CH$_3$ (trans) | B | −85° (5% NaHCO$_3$) | 295 (pH 6 buffer) | 26,800 | 1780 | 0.33 | 4.05 | 7.90; 8.25 |
| 39 | >C(CH$_3$)$_2$ | —CH=CHCO$_2$CH$_3$ (trans) | B | −104.4 (5% NaHCO$_3$) | 295 (pH 6 buffer) | 27,200 | 1779 | 0.34 | 4.09 | 8.52; 8.60 |

EXAMPLES 40–43

General Procedure for the Preparation of (6R,7R)-3-(substituted)-7-[2-(carboxy-R$^q$-oxyimino)-2-(fur-2-yl)acetamido]-ceph-3-em-4-carboxylic Acids (syn-isomers) by Treating an Ester of a (6R,7R)-3-(substituted) 7-aminoceph-3-em-4-carboxylic Acid with an Acid Chloride (syn-isomer)

A 2-(t-butoxycarbonyl-R$^q$-oxyimino)-2-(fur-2-yl)acetic acid (syn-isomer) was converted into its acid chloride as described for Examples 2–24. A solution of the acid chloride (1–1.3 equiv) in methylene chloride was added dropwise at −5° to +5° over a period of 10–30 minutes to a solution of diphenylmethyl (6R,7R)-3-(substituted)-7-aminoceph-3-em-4-carboxylate (1 equiv) in dry methylene chloride containing propylene oxide (5–20 equiv). The reaction mixture was stirred for ca 1–3 hours at 0° to room temperature and then washed successively with 2N-hydrochloric acid, aqueous sodium bicarbonate, water and/or brine. The dried organic layer was evaporated and the residue purified by trituration, precipitation, chromatography or crystallisation.

The resulting diphenylmethyl (6R,7R)-3-(substituted)-7-[2-(t-butoxycarbonyl-R$^q$-oxyimino)-2-(fur-2-yl)-acetamide]ceph-3-em-4-carboxylate (syn isomer) was deprotected as described for the diesters described in Examples 29–39, Methods A and B. Products are listed in Table 6.

TABLE 6

| Ex. No. | R$^q$ | P | Method | $[\alpha]_D$ (solvent) | $\lambda_{max}$, nm (pH 6 buffer) | $\epsilon$ | β-lactam $\nu_{max}$ cm$^{-1}$ (Nujol) | τ values for d$_6$-DMSO at 100 MHz | | |
|---|---|---|---|---|---|---|---|---|---|---|
| | | | | | | | | x | y | R$^q$ |
| 40 | —CH$_2$— | —CH=CHCO$_2$Et (trans) | B | — | 294.5 | 26,300 | 1780 | 0.12 | 4.04 | 5.30 |
| 41 | —CH$_2$— | —CH=CHCN | B | — | 291.5 | 21,800 | 1785 | 0.08 | 4.01 | 5.29 |
| 42 | —CH$_2$— | CH$_2$S—(1H-tetrazolyl) | A | −38° (DMSO) | 277.5 | 23,600 | 1775 | 0.21 | 4.19 | 5.30 |

TABLE 6-continued

| Ex. No. | $R^q$ | P | Method | $[\alpha]_D$ (solvent) | $\lambda_{max}$, nm (pH 6 buffer) | $\epsilon$ | β-lactam $\nu_{max}$ cm$^{-1}$ (Nujol) | τ values for d$_6$-DMSO at 100 MHz | | |
|---|---|---|---|---|---|---|---|---|---|---|
| | | | | | | | | x | y | $R^q$ |
| 43 | (isopropylidene) | $-CH_2S-\underset{\underset{CH_3}{|}}{N}\!\!\overset{N-N}{\underset{N}{\diagdown}}$ | A | −97.3° (CHCl₃) | 279 | | 1782 | 0.32 | 4.11 | 7.6; 8.1 |

EXAMPLE 44

(a)
(6R,7R)-3-Benzoyloxymethyl-7-[2-(2-t-butoxy-carbonylprop-2-yloxyimino)-2-(fur-2-yl)acetamido]ceph-3-em-4-carboxylic acid (syn isomer)

A suspension of phosphorous pentachloride (313 mg) in dry dichloromethane (4 ml) at −10° was treated with N,N-dimethylacetamide (0.7 ml) followed by 2-(2-t-butoxy-carbonylprop-2-yloxyimino)-2-(fur-2-yl) acetic acid (syn isomer) (446 mg) portionwise. The resulting solution was stirred at −10° for 30 minutes, treated with ice (ca 1 g) and stirred at below 0° for 15 minutes. The organic phase was added dropwise to a solution of (6R,7R)-7-amino-3-benzoyloxymethylceph-3-em-4-carboxylic acid (502 mg) in N,N-dimethylacetamide (2 ml) and acetonitrile (2 ml) containing triethylamine (1.09 ml) at below 0°. The solution was stirred at 0° to 5° for 2 hours, methanol (0.3 ml) was added, and stirring was continued for 15 minutes. The solution was diluted with dichloromethane (20 ml) and washed successively with 2N-hydrochloric acid, water and brine, dried and evaporated to a gum (1.02 g). A solution of this gum in ethyl acetate (6 ml) was run dropwise into stirred petroleum ether (b.p. 40°-60°, 200 ml) to give the title acid as a cream powder (769 mg, 83%); $[\alpha]_D$ + 26° (c 1.05, acetone); $\lambda_{max}$(pH 6 phosphate buffer) 233.5 nm ($\epsilon$ 19,200) and 274 nm ($\epsilon$ 18,600); $\nu_{max}$ (Nujol) 1790 cm$^{-1}$ (β-lactam); τ (d₆-DMSO) values include 0.29 (d, J 8 Hz, N$\underline{H}$), 4.03 (dd, J 8 and J 5 Hz, 7-$\underline{H}$), 8.50 (s, C(C$\underline{H}_3$)₂) and 8.58 (s, C(C$\underline{H}_3$)₃.

(b)
(6R,7R)-3(ϵ7[2-(2-carboxyprop-2-yloxyimino)-2-(fur-2-yl)acetamido]ceph-3-em-4-carboxylic acid (syn isomer)

A solution of (6R,7R)-3-benzoyloxymethyl-7-[2-(2-t-butoxycarbonylprop-2-yloxyimino)-2-(fur-2-yl)acetamido]-ceph-3-em-4-carboxylic acid (syn isomer) (620 mg) in anisole (0.6 ml) and trifluoroacetic acid (3 ml) was stirred at 20° for 25 minutes. The solution was partitioned between ethyl acetate and aqueous sodium bicarbonate solution and the pH adjusted to pH 8 by addition of solid sodium bicarbonate. The aqueous phase was separated, washed with ethyl acetate, covered with ethyl acetate, and the pH adjusted to pH 1.5 by addition of concentrated hydrochloric acid. The organic phase was separated, washed successively with water and brine, dried and evaporated to an oily foam (584 mg). A solution of this foam in ethyl acetate was run dropwise into stirred petroleum ether (b.p. 40°-60°) to give the title dicarboxylic acid as an off-white solid (384 mg, 67%); $[\alpha]_D$ + 30.4° (c 1,0, acetone); $\lambda_{max}$(pH 6 phosphate buffer) 234 nm 1$\epsilon$ 19,700) and 273 nm ($\epsilon$ 18,450); $\nu_{max}$ (Nujol) 1784 cm$^{-1}$ (β-lactam); τ (d₆-DMSO) values include 0.30 (d, J8 Hz, N$\underline{H}$), 4.07 (dd, J8 and J5Hz, 7-$\underline{H}$), and 8.50 (s, C(C$\underline{H}_3$)₂).

EXAMPLE 45

Potassium (6R,7R)-7-[2-carboxymethoxyimino-2-(fur-2-yl) acetamido]-3-pyridiniummethyl-ceph-3-em-4-carboxylate (syn isomer)

A mixture of (6R,7R)-3-acetoxymethyl-7-[2-carboxymethoxyimino-2-(fur-2-yl)acetamido]ceph-3-em-4-carboxylate (syn isomer) (3.26 g), potassium thiocyanate (5.25 g), pyridine (0.72 ml) and water (2 ml) was stirred and heated for 40 minutes at 80°. The cooled reaction mixture was diluted with water (5 ml) and adsorbed on a column of XAD-2 resin (500 g). Components of the reaction mixture were eluted, first with water and then with aqueous ethanol (1:3) and collected using an automatic fraction collector. Those fractions having the characteristic ultraviolet absorption pattern of the required product were combined and evaporated to dryness in vacuo at <35°. The crude material (600 mg) was crystallised from aqueous acetone (1:9) to give the title compound (295 mg); $\lambda_{max}$ (pH 6 phosphate buffer) 261 nm ($\epsilon$ 19,000); $\lambda_{infl}$ 275 nm ($\epsilon$ 18,400).

EXAMPLE 46

Potassium (6R,7R)-7-[2-carboxyprop-2-yloxyimino-2-(fur-2-yl)-acetamido]-3-pyridiniummethyl-ceph-3-em-4-carboxylate (syn isomer)

A mixture of (6R,7R)-3-acetoxymethyl-7-[2-(carboxyprop-2-yloxyimino)-2-(fur-2-yl)acetamido]ceph-3-em-4-carboxylic acid (syn isomer) (4.0 g), pyridine (4 ml) and water (40 ml) was heated for 1 hour at 80°, whereafter the mixture was allowed to cool. The cooled mixture was diluted with water (50 ml) and extracted five times with methylene chloride (25 ml) and the combined organic extracts were washed with water. The combined aqueous phases were evaporated in vacuo at <35° to ca 50 ml and acidified to pH 2 with 2N-hydrochloric acid. The precipitated solid was removed by filtration, the filtrate was adjusted to pH 6.5 with potassium bicarbonate and the solution was concentrated in vacuo at <35° to ca. 40 ml. The product was purified on a column of XAD-2 resin (500 g), elution being effected with water and then aqueous ethanol (1:3). Fractions having the characteristic ultraviolet absorption of the product were combined and evaporated to dryness in vacuo at <35° to give the title compound (880 mg),$\lambda_{max}$(H$_2$O) 261 and 277 nm ($\epsilon$ 17,000 and 16,950).

EXAMPLE 47

Sodium (6R,7R)-7-[2-(carboxyprop-2-yloxyimino)-2-(fur-2-yl)acetamido]-3-pyridiniummethylceph-3-em-4-carboxylate (syn isomer)

A mixture of sodium iodide (50.0 g), water (15.5 ml) and pyridine (14 ml) was heated to 80° and stirred vigorously during the addition over a periord of ca 10 minutes of (6R,7R)-3-acetoxymethyl-7-[2-(carboxyprop-2-yloxyimino)-2-(fur-2-yl)acetamido]ceph-3-em-4-carboxylate (syn isomer) (14.4 g). The mixture was stirred at 80° for a total of 55 minutes and was then cooled and diluted to ca 400 ml with water. 0.1 N-Sodium hydroxide was added to adjust the pH to ca 6.5 and the solution was concentrated under reduced pressure at <40° to a volume of ca 100 ml. The resulting solution was diluted to ca 400 ml with water, methyl isobutyl ketone (0.3 ml) was added and the stirred solution was acidified with 2N-hydrochloric acid (15 ml) to achieve a pH of 1-2. The solid was collected, washed with water and discarded. The filtrate and washings were treated with more 2N-hydrochloric acid (ca 10 ml) and extracted with ethyl acetate, the organic layer being re-extracted with a small volume of water. The aqueous phase was adjusted to ph 6 with 1N-sodium hydroxide (ca 43 ml) and evaporated under reduced pressure at <40° to a volume of ca 175 ml. This solution was applied to a column of XAD-2 resin (700 g, 42 cm × 5.5 cm) that had previously been washed with water (2 liters). The column was eluted with water, the fractions being collected automatically and monitored by U.V. spectroscopy. When the inorganic salts and some impurities had been removed the eluant was changed to a mixture of ethanol and water (1:4). The fractions having the characteristic U.V. absorption of the product were combined, concentrated under reduced pressure at <40° then freeze-dried. The product was dried over phosphorus pentoxide in vacuo giveing the title salt (4.10 g); $[\alpha]_D$ + 10.5° (c 1.00, H$_2$O); $\lambda_{max}$(pH 6 buffer) 261.5 and 278.5 nm ($\epsilon$ 20,100; 19,200); $\nu_{max}$(Nujol) 1770 cm$^{-1}$ ($\beta$-lactam); (D$_2$O, 100 MHz) values include 1.03, 1.43, 1.91 (pyridinium protons), 4.12 (dd, 7-$\underline{H}$) and 8.50 (s, C(C$\underline{H}_3$)$_2$).

EXAMPLE 48-52

In the manner of Example 47 the acetoxy group of (6R,7R)-3-acetoxymethyl-7-[2-(carboxy-R$^q$-oxyimino)-2-(fur-2-yl)acetamido]ceph-3-em-4-carboxylic acids (syn isomers) were displayed by treatment with pyridine or a substituted pyridine in aqueous sodium iodide solution at 80° for 45-60 minutes. The products were purified as the sodium salts by XAD-2 chromatography and their physical properties are summarised in Table 7.

TABLE 7

| Ex. No. | R$^q$ | P | Salt | $[\alpha]_D$ | $\lambda_{max}$ nm (pH 6 buffer) | $\epsilon$ | $\beta$-lactam $\nu_{max}$ cm$^{-1}$ (Nujol) | $\tau$ values for D$_2$O at 100 MHz x | y | R$^q$ |
|---|---|---|---|---|---|---|---|---|---|---|
| 48 | —CH$_2$— | CH$_2$—N$^+$(pyridinium) | monosodium | — | 260.5 / 278 | 14,500 / 14,100 | — | — | 4.16 | 5.45 |
| 49 | >C(CH$_3$)$_2$ | CH$_2$N$^+$(pyridinium)CONH$_2$ | monosodium | — | — | — | — | — | 4.11 | 8.48 |
| 50 | >C(CH$_3$)$_2$ | CH$_2$N$^+$(pyridinium)CH$_2$CO$_2$Na | disodium | — | 270.5 | 19,100 | — | — | 4.11 | 8.48 |
| 51 | (cyclopentyl) | CH$_2$N$^+$(pyridinium) | monosodium | — | 260.5 / 280.5 | 19,100 / 19,100 | — | — | 4.16 | 7.92; 8.30 |
| 52 | (cyclobutyl) | CH$_2$N$^+$(pyridinium) | monosodium | +14° (H$_2$O) | 260 / 280.5 | 19,400 / 18,550 | 1770 | — | 4.11 | 7.58; 8.03 |

EXAMPLE 53

(6R,7R)-7-[2-(2-Carboxyprop-2-yloximino)-2-(fur-2-yl)acetamido]-3-pyridaziniummethylceph-3-em-4-carboxylic Acid trifluoroacetate (syn isomer)

(a) A suspension of diphenylmethyl (1S,6R,7R)-3-bromomethyl-7-[2-(2-t-butoxycarbonylprop-2-yloxyimino)-2-(fur-2-yl)acetamido]ceph-3-em-4-carboxylate 1-oxide (syn isomer) (1.51 g) in N,N-dimethylformamide (1 ml) was treated with pyridazine (400 mg). The mixture was stirred for 2 hours at 25° to give a clear solution, which was then diluted with ether (50 ml, added slowly with stirring). The resulting precipitate was filtered off, washed with ether and dried to give diphenylmethyl (1S,6R,7R)-7-[2-(2-t-butoxycarbonylprop-2-yloxyimino)-2-(fur-2-yl)acetamido]-3-pyridaziniummethylceph-3-em-4-carboxylate 1-oxide bromide (syn isomer) as a pink powder (1.59 g, 94%); $[\alpha]_D$ + 13° (c 1.07, DMSO); $\lambda_{max}$ (EtOH) 277 nm ($\epsilon$ 21,200); $\lambda_{max}$ (Nujol) 1790 cm$^{-1}$ ($\beta$-lactam); $\tau$ (d$_6$-DMSO) values include 1.21 (d, J 8Hz, N$\underline{H}$), 3.76 (dd, J 4 and 8Hz, 7-$\underline{H}$), 8.51 (s, C(C$\underline{H}_3$)$_2$) and 8.61 (s, C(C$\underline{H}_3$)$_3$).

(b) The product of (a) above (1.49 g) in N,N-dimethylformamide (5 ml) at −10° was treated with potassium iodide (1.33 g) and then with acetyl chloride (0.28 ml). The mixture was stirred for 1 hour while the temperature slowly rose to 0°, and was then added dropwise to a stirred solution of sodium metabisulphite (1 g) in water (50 ml). The resulting suspension was stirred for 10 minutes and then the solid material was filtered off, washed with water and dried over phosphorus pentoxide to give a light brown powder (1.28 g). This material, is acetone : ethanol = 9 :1 (20 ml), was passed down a column of Deacidite FF resin (trifluoroacetate form, 15 cm × 2.5 cm i.d.) which was eluted with the same solvent mixture. Eluant fractions containing ultraviolet light absorbing material were combined and evaporated, and the residue was triturated with ether to give diphenylmethyl (6R,7R)-7-[2-(2-t-butoxycarbonylprop-2-yloxyimino)-2-(fur-2-yl)acetamido]-3-pyridaziniummethylceph-3-em-4-carboxylate trifluoroacetate (syn isomer), (1.24 g, 82%); $[\alpha]_D$ −20° (c 0.76, DMSO); $\lambda_{max}$ (EtOH) 278 nm ($\epsilon$ 18,300); $\nu_{max}$ (Nujol) 1780 cm$^{-1}$; $\tau$ (d$_6$-DMSO) values include 0.30 (d, J8Hz, N$\underline{H}$), 3.95 (dd, J 5 and 8 Hz, 7-$\underline{H}$), 8.55 (s, C(C$\underline{H}_3$)$_2$) and 8.59 (s, C(C$\underline{H}_3$)$_3$).

(c) The product of (b) above (1.13 g), mixed with anisole (1.5 ml), was treated with trifluoroacetic acid (6 ml) at 5° for 5 minutes, and then at 20° for 55 minutes. The solution was evaporated in vacuo, the residue was stirred with ethyl acetate, and the evaporation repeated. The resulting gum was triturated with ether to give the crude product as a pale brown solid, which was filtered off, washed with ether and dried. This was extracted with water (3 × 150 ml); the extracts were filtered, washed with ethyl acetate and then ether, and finally freze-dried. The combined residues were triturated with ether to give the title salt as a white powder (586 mg, 72%); $[\alpha]_D$ + 48° (c 0.98, DMSO); $\lambda_{max}$ (pH 6 phosphate buffer) 277 nm ($\epsilon$ 18,100); $\nu_{max}$ (Nujol) 1776 cm$^{-1}$ ($\beta$-lactam); $\tau$ (d$_6$-DMSO) 0.37 (d J 8 Hz, N$\underline{H}$), 4.9 (dd, J 5 and 8 Hz, 7-$\underline{H}$) and 8.53 (s, C(C$\underline{H}_3$)$_2$).

EXAMPLES 54-59

The trifluoroacetate salts listed in Table 8 were prepared by reacting the 3-bromomethyl ester (see below) with the appropriate tertiary base (or quaternary mercaptan for Example 56), reducing the sulphoxide and removing both protecting groups in a similar manner to that described in Example 53. The starting material was prepared as follows:

A solution of phosphorus pentachloride (5.20 g) in dry dichloromethane (60 ml) at −10° was treated with N,N-dimethylacetamide (12 ml), and then with 2-(2-t-butoxycarbonylprop-2-yloxyimino)-2-(fur-2-yl)acetic acid (syn isomer) (6.43 g) added portionwise. The solution was stirred at −10° for 15 minutes and then ice (14 g) was slowly added and the temperature allowed to rise to 0° over 10 minutes. The organic layer was separated and added dropwise to a suspension of diphenylmethyl (1S,6R,7R)-7-amino-3-bromomethylceph-3-em-4-carboxylate 1-oxide hydrobromide (10.62 g) in dichloromethane (80 ml) containing propylene oxide (15 ml) at 0°. The mixture was stirred for 1 hour during which time the temperature rose to 20° and the suspension cleared. The resulting yellow solution was washed with 2.5% aqueous sodium bicarbonate solution (50 ml) and then 2N-hydrochloric acid (50 ml), whereafter the solution was dried and evaporated to a yellow oil. This material, in ethyl acetate (20 ml), was added dropwise to stirred petrol (b.p. 40°-60°) to give a gummy precipitate. The supernatant was decanted off and the gum chromatographed on a column of Kieselgel, which was eluted with dichloromethane containing from 0 to 10% acetone. Eluant fractions containing the main product were combined and evaporated to a foam. Trituration with cyclohexane gave diphenylmethyl (1S,6R,7R)-3-bromomethyl-7-[2-(2-t-butoxycarbonylprop-2-yloxyimino)-2-(fur-2-yl)acetamido]ceph-3-em-4-carboxylate 1-oxide (syn isomer) as a pale yellow microcrystalline powder (13.61 g, 90%); $[\alpha]_D$ − 22° (c 1.0, DMSO); $\lambda_{max}$ (EtOH) 281 nm ($\epsilon$ 22,200); $\nu_{max}$ (CHBr$_3$) 1800 cm$^{-1}$ ($\beta$-lactam); $\tau$ (d$_6$ DMSO) values include 1.26 (d, J 8 Hz, N$\underline{H}$), 3.86 (dd, J 4 and 8 Hz, 7-$\underline{H}$), 8.51 (s, C(C$\underline{H}_3$)$_2$) and 8.61 (s, C(CH$_3$)$_3$).

TABLE 8

[Structure: furan-C(=N-O-R^q-CO_2H)-CONH-(x)H—(y)H—S—cephem ring with CO_2H and P substituent]

| Ex. No. | R^q | P | Salt | $[\alpha]_D$ (DMSO) | $\lambda_{max}$, nm (pH 6 buffer) | $\epsilon$ | β-lactam $\nu_{max}$ cm$^{-1}$ (Nujol) | τ values* for d$_6$-DMSO at 100 MHz | | |
|---|---|---|---|---|---|---|---|---|---|---|
| | | | | | | | | x | y | R^q |
| 54 | >C(CH_3)_2 | CH_2N$^+$–phenyl–CONH_2 | trifluoro-acetate | −57.5° | 267 | 21,600 | 1775 | 0.38 | 4.11 | 8.55 |
| 55 | >C(CH_3)_2 | CH_2N$^+$–thiazole | trifluoro-acetate | −43.5° | 244 / 277 | 14,800 / 18,200 | 1784 | 0.4 | 4.14 | 8.54 |
| 56 | >C(CH_3)_2 | CH_2S–pyridinium–CH_3$^+$ | trifluoro-acetate | −14° | 277 | 21,500 | 1782 | 0.40 | 4.14 | 8.53 |
| 57 | >C(CH_3)_2 | CH_2N$^+$–phenyl–SO_3H | trifluoro-acetate | −58° | 267 | 22,200 | 1780 | 0.29 | 4.05 | 8.55 |
| 58 | C(CH_3)_2 | CH_2N$^+$–pyridyl–N–CH_3 | trifluoro-acetate | −79° | 225.5 / 271 | 16,100 / 18,400 | 1778 | 0.38 | 4.12 | 8.50 |
| 59 | C(CH_3)_2 | CH_2N$^+$–imidazole–N–CH_3 | trifluoro-acetate | −32° | 274 | 18,100 | 1713 | 0.40 | 4.11 | 8.53 |

*Values for the trifluoroacetate salt

EXAMPLE 60

(6R,7R)-3-(Benzotriazol(-1-ylmethyl)-7-[2-(2-carboxyprop-2-yloxyimino)-2-(fur-2-yl)acetamido]ceph-3-em-4-carboxylic acid (syn isomer)

Diphenylmethyl (1S,6R,7R)-3-bromomethyl-7-[2-(2-t-butoxycarbonylprop-2-yloxyimino)-2-(fur-2-yl)acetamido]ceph-3-em-4-carboxylate 1-oxide (syn isomer) (1.51 g) in N,N-diethylformamide (3 ml) was stirred with benzotriazole (480 mg) for 4 days. The solution was diluted with dichlormethane and then washed twice with 2N-hydrochloric acid; the solution was then dried and evaporated, and the main product was isolated from the residue by column chromatography on Kieselgel, with chloroform containing 0 to 10% v/v acetone for elution. This material (700 mg) in N,N-dimethylformamide (2ml) with potassium iodide (665 mg) at −10° was treated with acetyl chloride (0.14 ml). The suspension was stirred for 1.25 hours and allowed to warm slowly to 0°, and was then added dropwise to water (40 ml) containing sodium metabisulphite (0.5 g). The precipitate was filtered off, washed with water, dried, and purified by chromatography on Kieselgel, eluting with dichloromethane containing from 0 to 3% v/v acetone.

The diester so obtained (520 mg), together with anisole (0.5 ml), was treated with trifluoroacetic acid (2 ml) at 25° for 1 hour. The solution was then added dropwise with stirring to saturated aqueous sodium bicarbonate (50 ml) and ice (25 g). The mixture was stirred, whereafter ethyl acetate was added. The aqueous layer was separated and acidified under ethyl acetate to pH 2. The organic layer was separated, and the aqueous layer extracted with more ethyl acetate. The combined extracts were dried and concentrated to an oil, which was added dropwise to stirred petrol (b.p. 40°-60°). The white precipitate was filtered off, washed with petrol and dried to give the title dicarboxylic acid as a white powder (350 mg, 31%); $[\alpha]_D$ + 37° (c 102, DMSO); $\lambda_{max}$ (pH 6 phosphate buffer) 269 nm ($\epsilon$ 23,600); $\nu_{max}$ (Nujol) 1780 cm$^{-1}$ (β-lactam); τ (d$_6$-DMSO) values include 0.40 (d, J 8 Hz, NH), 4.11 (dd, J 5 and 8 Hz, 7-H) and 8.53 (s, C(CH_3)_2).

EXAMPLE 61

The compound listed in Table 9 was prepared from the appropriate nucleophile using the method of Example 60.

TABLE 9

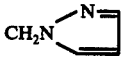

| Ex. No. | $R^2$ | P | Salt | $[\alpha]_D$ (DMSO) | $\lambda_{max}$ nm (pH 6 buffer) | $\epsilon$ | β-lactam $\nu_{max}$ cm$^{-1}$ (Nujol) | τ values for $d_6$-DMSO at 100 MHz | | |
|---|---|---|---|---|---|---|---|---|---|---|
| | | | | | | | | x | y | $R^q$ |
| 61 | >C(CH$_3$)$_2$ | CH$_2$N⟨N= | — | +2° | 272 | 18,100 | 1780 | 0.41 | 4.11 | 8.52 |

EXAMPLE 62

Pivaloyloxymethyl (6R,7R)-3-carbamoyloxymethyl-7-[2-carboxymethoxyimino-2-(fur-2-yl)acetamido]ceph-3-em-4-carboxylate (syn isomer)

A stirred solution of sodium (6R,7R)-3-carbamoyloxymethyl-7-[2-t-butoxycarbonylmethoxyimino)-2-(fur-2-yl)acetamido]ceph-3-em-4-carboxylate (syn isomer) (8.50 g) in dimethylformamide (100 ml) was treated with chloromethyl pivalate (4.86 ml). The solution was stirred at room temperature for 25 hours and partitioned between ethyl acetate and water. The aqueous layer was further extracted with ethyl acetate, and the combined extracts were washed successively with brine, saturated sodium bicarbonate solution and brine, and were then dried and evaporated to a small volume. The residue was added slowly to stirred petrol (b.p. 40°-60°, 1.5 liters) and the precipitate collected, washed with petroleumspirit and dried in vacuo to afford a mixture of the t-lautyl esters of the title compound and its $\Delta^2$ analogue (8.32 g), (Ratio $\Delta^2$ : $\Delta^3$ ~ 3:2 by p.m.r.)

A solution of this mixture of isomers (8.1 g) in dichloromethane (75 ml) was cooled to −40° and stirred during dropwise addition of m-chloroperbenzoic acid (2.41 g) in dichloromethane (65 ml). The solution was stirred at −40° for 1.25 hours and more m-chloroperbenzoic acid (1.2 g) in dichloromethane was added. After stirring for a further 40 minutes, the solvent was evaporated and the residue partitioned between ethyl acetate and brine. The ethyl acetate solution was washed with sodium bicarbonate solution and brine, dried over sodium sulphate and evaporated to a yellow froth (9.77 g). This was triturated with ether and a yellow solid filtered off, washed with ether and dried in vacuo to afford the 1-oxide of the t-butyl ester of the title compound (7.27 g).

A solution of this sulphoxide (7.07 g) and potassium iodide (14.34 g) in dimethylformamide (100 ml) was surrounded by an ice-salt bath and stirred during the addition of acetyl chloride (3.08 ml) in dimethylformamide (15 ml). The solution was stirred for 3.5 hours and more acetyl chloride (1.54 ml) in dimethylformamide added. The solution was stirred for 1 hour and partitioned between sodium metabisulphite solution and ethyl acetate. The organic layer was washed with sodium metabisulphite solution and water, and was then dried and evaporated to a small volume. The resulting solution was added slowly to excess stirred petrol (b.p. 40°-60°) and the resulting precipitate was collected, washed with petroleum spirit and dried in vacuo to afford pivaloyloxymethyl (6R, 7R)-3-carbamoyloxymethyl-7-[2-t-butoxycarbonylmethoxyimino-2-(fur-2-yl)acetamido]ceph-3-em-4-carboxylate (syn isomer) (7 g); $\lambda_{max}$ (EtOH) 277 nm ($\epsilon$ 16,540); $\nu_{max}$ (Nujol) 1782 (β-lactam), 1740 and 1720 cm$^{-1}$ (CONH$_2$); τ (d$_6$-DMSO) values include 0.25 (d, N$\underline{H}$), 3.40 (s, N$\underline{H}_2$) and 8.8 (s, C(C$\underline{H}_3$)$_3$).

The above diester (1.0 g) was dissolved in trifluoroacetic acid (5 ml), and this solution was stirred at room temperature for 15 minutes and was then diluted with ether, washed with water and evaporated. The residue was partitioned between ethyl acetate and sodium bicarbonate solution, and the organic layer was extracted again with sodium bicarbonate solution. The combined aqueous extracts were washed with ethyl acetate, acidified with 2N-hydrochloric acid and extracted with ethyl acetate. The extracts were washed with water, dried, and evaporated to give an oil. This was dissolved in a small volum of ethyl acetate and added slowly to an excess of stirred petrol (b.p. 40°-60° ). The off-white precipitate was collected, washed with petroleum spirit and dried in vacuo to afford the title ester (0.645 g); $\lambda_{max}$ (EtOH) 278 nm ($\epsilon$ 16,900); $\nu_{max}$ (Nujol) 1778 cm$^{-1}$ (β-lactam); τ (d$_6$-DMSO) values include 0.25 (d, N$\underline{H}$), 2.16, 3.26, 3.38 (fur-2-yl protons) and 4.10 (dd, 7-$\underline{H}$).

The sodium salt starting material for the above process was made as follows:

Triethylamine (2.58 ml) and dimethylformamide (2 drops) were added to a solution of 2-t-butoxycarbonylmethoxyimino-2-(fur-2-yl)acetic acid (syn isomer) (5 g) in dry dichloromethane (200 ml). The stirred solution was cooled to 0° and oxalyl chloride (1.58 ml) was added. The solution was stirred for 1 hour and then evaporated. The residue was suspended in acetone (150 ml) and added over 0.5 hours to a stirred ice-cold solution of (6R,7R)-3-carbamoyloxymethyl-7-aminoceph-3-em-4-carboxylic acid (5.08 g) in acetone (150 ml) and water (300 ml) containing sodium bicarbonate (3.74 g). The reaction mixture was stirred for 1 hour and evaporated to remove acetone. The aqueous residue was acidified under ether to pH 1.8 with dilute hydrochloric acid and the layers were separated. The aqueous layer was further extracted with ether and the combined extracts washed with water and brine, dried, and evaporated to afford (6R,7R)-3-carbamoyloxymethyl-7-[2-t-butoxycarbonylmethoxyimino-2-(fur-2-yl)acetamido]-ceph-3-em-4-carboxylic acid (syn isomer); $\lambda_{max}$ (pH 6 phosphate buffer) 274.5 nm ($\epsilon$ 17,520); $\nu_{max}$ (CHBr$_3$) 1785 (β-lactam), 1686 and 1530 cm$^{-1}$ (CONH); τ (d$_6$-

DMSO) values include 0.29 (d, NH), 4.19 (dd, 7-H) and 4.79 (d, 6-H).

A stirred solution of the above acid (9.02 g) in acetone (40 ml) was treated with a solution of sodium 2-ethylhexanoate (2.86 g) in acetone (40 ml). The resulting solution was added slowly to stirred petroleum spirit (1600 ml, b.p. 40°-60°) and the precipitate was collected, washed and dried in vacuo to afford sodium (6R,7R)-3-carbamoyloxymethyl-7-[2-t-butoxycarbonyl-methoxyimino-2-(fur-2-yl)acetamido]ceph-3-em-4-carboxylate (syn-isomer) (8.71 g); $\lambda_{max}$ (pH 6 buffer) 274.5 nm ($\epsilon$ 17,650); $\nu_{max}$ (Nujol) 1755 ($\beta$-lactam) and 1608 cm$^{-1}$(CO$_2$—); $\tau$ (d$_6$-DMSO) values include 0.4 (d, NH), 4.4 (dd, 7-H) and 4.98 (d, 6-H).

EXAMPLE 63

(1R,6R,7R)-3-Acetoxymethyl-7-[2-(2-carboxyprop-2-yloxyimino)-2-(fur-2-yl)acetamido]ceph-3-em-4-carboxylic acid 1-oxide (syn isomer)

(a) A solution of (6R,7R)-3-acetoxymethyl-7-[2-(2-carboxyprop-2-yloxyimino)-2-(fur-2-yl)acetamido]-ceph-3-em-4-carboxylic acid, di-t-butyl ester (syn isomer) (1.21 g) in pyridine (25 ml) and water (1 ml) at −45° was treated with t-butyl hypochlorite (0.3 ml) with vigorous stirring. After 2 minutes 2N-sulphurous acid (1 ml) was added to the solution and the mixture was immediately poured into aqueous phosphoric acid (100 ml, 20% v/v). The aqueous solution was extracted with ethyl acetate and the organic extracts were washed with 0.5N-hydrochloric acid (50 ml), aqueous sodium bicarbonate solution (50 ml) and water, then dried and concentrated in vacuo. The crude product was chromatographed on silica gel preparative plates, using ethyl acetate : petroleum ether (b.p. 60°-80°) (4:1) as eluant. The slower running band was extracted with ethyl acetate to yield the di-t-butyl ester of the title compound (505 mg); $\nu_{max}$(Nujol) 1798 ($\beta$-lactam), 1738, 1727, 1715 (acetate and CO$_2$,tBu), 1680 and 1542 cm$^{-1}$ (CONH); $\tau$ values (DMSO-d$_6$) include 0.28 (d, J 8 Hz, NH), 4.19 (dd, J 5 and 8 Hz, 7-H), 5.02 (d, J 5 Hz, 6-H), 5.71 and 6.38 (ABq, J 18 Hz, 2-H).

The di-t-butyl ester (0.38 g) in trifluoroacetic acid (5 ml, containing a few drops of anisole) was stirred at room temperature for 15 minutes. The solution was concentrated in vacuo to a red oil, diluted with ethyl acetate (2 ml) and added dropwise to vigorously stirred petroleum ether (b.p. 60°-80°) (50 ml). The deposited solid was collected, washed with ether (5 ml) and dried to yield the title acid (185 mg, 60%); $\lambda_{max}$ (ethanol) 276 nm ($\epsilon$ 16,600); $\nu_{max}$ (Nujol) 1790 ($\beta$-lactam), 1730 (acetate), 1720 (CO$_2$H), 1680 and 1523 (COHN) and 1040 cm$^{-1}$ (S → 0); $\tau$ values (DMSO-d$_6$) include 0.21 (d, J 8 Hz, NH), 4.17 (dd, J 5 and 8 Hz, 7-H), 5.01 (d, J 5 Hz, 6-H), 5.71 and 6.32 (ABq, J 18 Hz, 2-H), 8.49 (s, C(CH$_3$)$_2$).

The starting material for the above oxidation process was prepared as follows:

A solution of t-butyl (6R,7R)-7-amino-3-acetoxymethylceph-3-em-4-carboxylate (1.05 g) in dry dichloromethane ethane (10 ml) was added to a solution of 2-(2-t-butoxycarbonylprop-2-yloxyimino)-2-(fur-2-yl)acetic acid (syn isomer) (0.90 g) and dicyclohexylcarbodiimide (0.69 g) in dry dichloromethane (10 ml), and the mixture was stirred at room temperature for 1 hour. The solution was filtered and concentrated in vacuo. The crude product was passed down a column of silica gel (MFC, 100-200 mesh, 2 × 20 cm) using ethyl acetate : petroleum ether (b.p. 60°-80°) (1:1) as eluant. Combination of appropriate fractions as determined by thin layer chromatography yielded (6R,7R)-3-acetoxymethyl-7-[2-(2-carboxyprop-2-yloxyimino)-2-(fur-2-yl)acetamido]-ceph-3-em-4-carboxylic acid, di-t-butyl ester (syn isomer) (1.29 g); $\nu_{max}$(CHBr$_3$) 1776 ($\beta$-lactam), 1725, 1712 (acetate and CO$_2$.tBu), 1678 and 1512 cm$^{-1}$(CONH); $\tau$ (CDCl$_3$) values include 1.90 (d. J 8 Hz, NH), 4.08 (dd, J 5 and 8 Hz, 7-H) and 4.98 (d, J 5 Hz, 6-H).

EXAMPLE A

This example illustrates the formulation of a pharmaceutical composition.

Dry Powder for Injection

Sterile (6R,7R)-3-acetoxymethyl-7-[2-(1-carboxycyclopent-1-yloxyimino)-2-(fur-2-yl)acetamido]ceph-3-em-4-carboxylate disodium salt (syn isomer) is filled into glass vials, the claimed contents of each container being 500 mg or 1.00 g of the antibiotic as desired. Filling is carried out aseptically under a blanket of nitrogen. The vials are closed using rubber discs or plugs held in position by aluminium sealing rings, thereby preventing gaseous exchange or ingress of microorganisms. The product would be intended for reconstitution with Water for Injections or other suitable sterile vehicle shortly before administration.

We claim:

1. A compound selected from the group consisting of a cephalosporin antibiotic of the formula

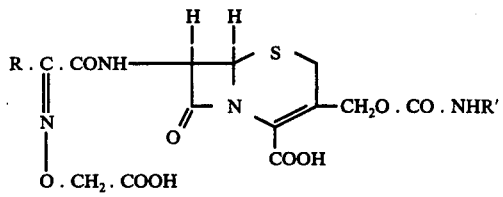

wherein

R is thienyl or furyl; and

R' is hydrogen or methyl and a physiologically acceptable salt, ester or 1-oxide thereof.

2. The compound of claim 1 which is (6R,7R)-3-carbamoyloxymethyl-7-[2-carboxymethoxyimino-2-(fur-2-yl) acetamido]ceph-3-em-4-carboxylic acid (syn isomer).

3. The compound of claim 1 which is disodium (6R,7R)-3-carbamoyloxymethyl-7-[2-carboxymethoxyimino-2-(thien-2-yl) acetamido]ceph-3-em-4-carboxylate (syn isomer).

4. Pivaloyloxymethyl (6R,7R)-3-carbamoyloxymethyl-7-[2-carboxymethoxyimino-2-(fur-2-yl)acetamido]ceph-3-em-4-carboxylate.

* * * * *